US008343460B2

(12) United States Patent
McBride et al.

(10) Patent No.: US 8,343,460 B2
(45) Date of Patent: *Jan. 1, 2013

(54) METHODS AND COMPOSITIONS FOR F-18 LABELING OF PROTEINS, PEPTIDES AND MOLECULES

(75) Inventors: William J. McBride, Boonton, NJ (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/408,580

(22) Filed: Feb. 29, 2012

(65) Prior Publication Data

US 2012/0214969 A1    Aug. 23, 2012

Related U.S. Application Data

(60) Division of application No. 12/485,998, filed on Jun. 17, 2009, now Pat. No. 8,153,101, which is a division of application No. 12/112,289, filed on Apr. 30, 2008, now Pat. No. 7,563,433, which is a continuation-in-part of application No. 11/960,262, filed on Dec. 19, 2007, now Pat. No. 7,597,876.

(60) Provisional application No. 60/884,521, filed on Jan. 11, 2007.

(51) Int. Cl.
*A61K 51/00* (2006.01)
*A61M 36/14* (2006.01)

(52) U.S. Cl. ..................................... 424/1.89

(58) Field of Classification Search .............. 424/1.11, 424/1.49, 1.65, 1.69, 1.73, 1.81, 1.85, 1.89, 424/9.1; 534/7, 10–16; 514/1, 1.11; 530/300
See application file for complete search history.

(56) References Cited

U.S. PATENT DOCUMENTS

| | | | |
|---|---|---|---|
| 5,256,395 A | 10/1993 | Barbet et al. | |
| 5,446,147 A | 8/1995 | Kung et al. | |
| 5,686,116 A | 11/1997 | Bockman et al. | |
| 6,019,957 A | 2/2000 | Miller et al. | |
| 6,056,939 A | 5/2000 | Desreux et al. | |
| 6,207,858 B1 | 3/2001 | Chinn et al. | |
| 6,605,615 B2 | 8/2003 | Medina et al. | |
| 6,838,073 B1 | 1/2005 | Collins et al. | |
| 6,953,567 B2 | 10/2005 | Griffiths | |
| 7,011,816 B2 | 3/2006 | Griffiths et al. | |
| 7,081,452 B2 | 7/2006 | Brechbiel et al. | |
| 7,163,935 B2 | 1/2007 | Brechbiel et al. | |
| 7,563,433 B2* | 7/2009 | McBride et al. | 424/1.89 |
| 7,597,876 B2* | 10/2009 | McBride et al. | 424/1.89 |
| 7,993,626 B2* | 8/2011 | McBride et al. | 424/1.89 |
| 8,147,799 B2* | 4/2012 | McBride et al. | 424/1.89 |
| 8,147,800 B2* | 4/2012 | McBride et al. | 424/1.89 |
| 8,153,100 B2* | 4/2012 | McBride et al. | 424/1.89 |
| 8,153,101 B2* | 4/2012 | McBride et al. | 424/1.89 |
| 8,202,509 B2* | 6/2012 | McBride et al. | 424/1.89 |
| 2002/0006379 A1 | 1/2002 | Hansen et al. | |
| 2003/0064523 A1 | 4/2003 | Popov et al. | |
| 2005/0136001 A1 | 6/2005 | McBride et al. | |
| 2006/0140858 A1 | 6/2006 | Goldenberg et al. | |
| 2006/0228300 A1 | 10/2006 | Chang et al. | |
| 2008/0027220 A1 | 1/2008 | Stossel et al. | |
| 2008/0038191 A1 | 2/2008 | Perrin et al. | |
| 2008/0089838 A1 | 4/2008 | Hansen et al. | |
| 2009/0155166 A1 | 6/2009 | McBride et al. | |

FOREIGN PATENT DOCUMENTS

| | | |
|---|---|---|
| WO | 2007027385 | 3/2007 |
| WO | 2008088648 | 7/2008 |
| WO | 2009079024 | 6/2009 |

OTHER PUBLICATIONS

Cai et al. "Chemistry with [18F]Fluoride Ion" Eur. J. Org. Chem. 2008, pp. 2853-2873.
Clark et al "The Preparation of Fuorine-18 Labelled Compounds Using a Recirculatory Neon Target" Radiochemical and Radioanalytical Letters, 1973, vol. 14, No. 2, pp. 101-108.
Imanori et al. "Fluorine-18-Labeled Fluoroboronophenylalanine PET in Patients with Glioma" J Nucl Med 1998; 39:325-333.
Karacay et al. "18F labeling of a peptide for PET imaging of receptor-expressing tumors" Abstract # 1567, 2009 SNM Annual Meeting Scientific Abstracts 50(Suppl. 2), p. 318P, May 2009.
Mamat et al. "Recent Applications of Click Chemistry for the Synthesis of Radiotracers for Molecular Imaging" Mini-Reviews in Organic Chemistry, 2009, vol. 6, pp. 21-34.
Marik et al. "Click for PET: rapid preparation of [18F]fluoropeptides using CuI catalyzed 1,3-dipolar cycloaddition" Tetrahedron Letters 47 (2006) 6681-6684.
McBride et al. "A new method of labeling peptides and proteins with F-18 via a metal ligand" Abstract #384, J Nucl Med. 2008; 49 (Supplement 1):97P.
McBride et al. "A new method of labeling peptides and proteins with F-18 via a metal ligand", PowerPoint Presentation, 55th SNM Annual Meeting, New Orleans, LA, Jun. 17, 2008.
McBride et al. "A New Method of Labeling Peptides with F-18 Via a Metal Ligand", Abstract #04, Cancer Biother Radiopharm Aug. 2008; 23(4): 514.

(Continued)

*Primary Examiner* — D L Jones
(74) *Attorney, Agent, or Firm* — Richard A. Nakashima

(57) ABSTRACT

The present application discloses compositions and methods of synthesis and use of F-18 labeled molecules of use in PET imaging. In particular embodiments, the labeled molecules may be peptides or proteins, although other types of molecules may be labeled and utilized. Preferably, the F-18 is attached to a targeting molecule by formation of a metal complex and binding of the F-18-metal complex to a chelating moiety. In other embodiments, the metal may first be attached to the chelating group and subsequently the F-18 bound to the metal. More preferably, the F-18 label moiety may be attached to a targetable conjugate that is used for pretargeting in combination with a bispecific or multispecific antibody. The F-18-metal labeled molecules are stable in human serum at 37° C.

23 Claims, 23 Drawing Sheets

OTHER PUBLICATIONS

McBride et al. "A New Method of Labeling Peptides with F-18 Via a Metal Ligand" Abstract #68, 19th Winter Fluorine Conference (Jan. 11-16, 2009) Abstract Book, p. 32.

McBride et al. "A New Method of Labeling Peptides with F-18 Via a Metal Ligand" PowerPoint Presentation, 19th Winter Fluorine Conference, St. Pete Beach, FL, Jan. 13, 2009.

McBride et al. "A novel method of radiolabeling peptides with aluminium-fluoride-18 (AlF-18) using various NOTA derivatives" Abstract # 202, 2009 SNM Annual Meeting Scientific Abstracts 50(Suppl. 2), pp. 52P-53P, May 2009.

Miller et al. "Synthesis of 11C, 18F, 15O, and 13N Radiolabels for Positron Emission Tomography" Angew. Chem. Int. Ed. 2008, vol. 47, pp. 8998-9033.

Murata et al., "Formation of the Stable Myosin-ADP-Aluminum Fluoride and Myosin-ADP-Beryllium Fluoride Complexes and Their Analysis Using 19F NMR", J. Biol. Chem. 268(10):7093-7100 (1993).

Schirrmacher et al. "Recent Developments and Trends in 18F-Radiochemistry: Syntheses and Applications" Mini-Reveiws in Organic Chemistry, 2007, vol. 4, pp. 317-329.

Schoffelen et al. "Pretargeted immunoPET for imaging colorectal cancer in a mouse model" Abstract # 381, 2009 NM Annual Meeting Scientific Abstracts 50(Suppl. 2), pp. 100P, May 2009.

Ting et al. "Toward [18F]-Labeled Aryltrifluoroborate Radiotracers: In Vivo Positron Emission Tomography Imaging of Stable Aryltrifluoroborate Clearance in Mice" J. Am. Chem. Soc. 2008, 130, 12045-12055.

Ting et al. "Arylfruoroborates and Alkylfluorosilicates as Potential PET Imaging Agents: High-Yielding Aqueous Biomolecular 18F-Labeling" J. Am. Chem. Soc. 2005, 127, 13094-13095.

Wagner, Henry N. "Advancing a Molecular Theory of Disease", J Nulc Med 49(8):15N-34N. (2008).

Wester et al. "Fluorine-18 Labeling of Peptides and Proteins", Review, Ernst Schering Res. Found. Workshop 62:79-111 (2007).

* cited by examiner

IMP 272

IMP 288

IMP 326

IMP 329

IMP 331

IMP 332

IMP 333

IMP 334

IMP 349

IMP 368

IMP 375

IMP 384

IMP 386

IMP 389

IMP 449

IMP 422   MH+ 1657

IMP 426   MH+ 1596

IMP 428   MH+ 1716

IMP 460 NODA-GA-D-Ala-D-Lys(HSG)-D-Tyr-D-Lys(HSG)-NH$_2$   MH$^+$ 1366

(A)

C-NETA (B)

ITC-C-NETA (C)

(D)

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Modified peptide:
      DOTA-Phe-Lys(HSG)-Tyr-Lys(HSG)-NH2

<400> SEQUENCE: 1

Phe Lys Tyr Lys
1
```

```
<210> SEQ ID NO 2
<211> LENGTH: 4
<212> TYPE: PRT
<213> ORGANISM: Artificial
<220> FEATURE:
<223> OTHER INFORMATION: Modified peptide:
      Ac-Lys(DTPA)-Tyr-Lys(DTPA)-Lys(Tscg-Cys)-NH2

<400> SEQUENCE: 2

Lys Tyr Lys Lys
1
```

METHODS AND COMPOSITIONS FOR F-18 LABELING OF PROTEINS, PEPTIDES AND MOLECULES

RELATED APPLICATIONS

This application is a divisional of U.S. patent application Ser. No. 12/485,998, filed Jun. 7, 2009, which is a divisional of U.S. patent application Ser. No. 12/112,289 (now U.S. Pat. No. 7,563,433), filed Apr. 30, 2009, which is a continuation-in-part of U.S. patent application Ser. No. 11/960,262 (now U.S. Pat. No. 7,597,876), filed Dec. 19, 2007, which claimed the benefit under 35 U.S.C. §119(e) of Provisional U.S. Patent Application No. 60/884,521, filed Jan. 11, 2007, each of which is incorporated herein by reference in its entirety.

FIELD

In certain embodiments, the present invention concerns a simple method of labeling peptides with F-18, which are of use for in-vivo imaging. The preferred specific activity of the F-18 labeled peptide would be about 1,000 to 2,000 Ci/mmol at the time of administration to the patient. Specific activities that are in the range of 100 to tens of thousands of Ci/mmol would also be of use. Although higher specific activities are preferred for certain imaging applications, in other alternative embodiments a lower specific activity of a metal-F-18 complex with NOTA (1,4,7-triaza-cyclononane-N,N',N''-triacetic acid) or another chelating moiety could be of use, for example, as a renal flow imaging agent or for heart and brain imaging agents to image blood flow. Preferably, F-18 labeling is accomplished without need for a purification step to separate unlabeled from labeled peptide. More preferably, F-18 labeled peptides are stable under in vivo conditions, such as in human serum.

BACKGROUND

Positron Emission Tomography (PET) imaging provides high resolution and quantitation from the PET images. Peptides or other small molecules can be labeled with the positron emitters $^{18}$F, $^{64}$Cu, $^{66}$Ga, $^{68}$Ga, $^{76}$Br, $^{94m}$Tc, $^{86}$Y, and $^{124}$I to name a few. The positron emitted from the nucleus of the isotope is ejected with different energies depending on the isotope used. When the positron reacts with an electron two 511 keV gamma rays are emitted in opposite directions. The energy of the ejected positron controls the average distance that a positron travels before it is annihilated by hitting an electron. The higher the ejection energy the further the positron travels before the collision with an electron. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized.

The half-life of the isotope is also important, since the half-life must be long enough to attach the isotope to a targeting molecule, analyze the product, inject it into the patient, and allow the product to localize, clear from non-target tissues and then image. If the half-life is too long the specific activity may not be high enough to obtain enough photons for a clear image and if it is too short the time needed for manufacturing, commercial distribution and biodistribution may not be sufficient. F-18 ($\beta^+$ 635 keV 97%, $t_{1/2}$ 110 min) is one of the most widely used PET emitting isotopes because of its low positron emission energy, lack of side emissions and suitable half-life. The F-18 is produced with a high specific activity. When an isotope is attached to a molecule for targeting it is usually accompanied by some unreacted targeting agent, which is often present in a large molar excess compared to the radiolabeled product. Usually, the labeled product and the unlabeled product can compete for the same target in-vivo so the presence of the cold targeting agent lowers the effective specific activity of the targeting agent. If the F-18 is attached to a molecule which has a very high uptake such as 2-fluoro-2-deoxy glucose (FDG) then effective specific activity is not as important. However, if one is targeting a receptor with a labeled peptide or performing an immunoPET pretargeting study with a limited number of binding sites available, the cold targeting agent could potentially block the uptake of the radiolabeled targeting agent if the cold targeting agent is present in excess.

Conventional F-18 labeling of peptides involves the labeling of a reagent at low specific activity, HPLC purification of the reagent and then conjugation to the peptide of interest. The conjugate is often repurified after conjugation to obtain the desired specific activity of labeled peptide. An example is the labeling method of Poethko et al. (*J. Nucl. Med.* 2004; 45: 892-902) in which 4-[$^{18}$F]fluorobenzaldehyde is first synthesized and purified (Wilson et al, *J. Labeled Compounds and Radiopharm.* 1990; XXVIII: 1189-1199) and then conjugated to the peptide. The peptide conjugate is then purified by HPLC to remove excess peptide that was used to drive the conjugation to completion. The two reactions and purification would not be a problem if F-18 had a long half-life. However the half-life of F-18 is only 2 hr so all of the manipulations that are needed to attach the F-18 to the peptide are a significant burden.

These methods are tedious to perform and require the use of equipment designed specifically to produce the labeled product and/or the efforts of specialized professional chemists. They are not kit formulations that could routinely be used in a clinical setting. A need exists for a rapid, simple method of 18-F-labeling of targeting moieties, such as proteins or peptides, that results in targeting constructs of suitable specific activity and in vivo stability for detection and/or imaging, while minimizing the requirements for specialized equipment or highly trained personnel and reducing operator exposure to high levels of radiation. A further need exists for prepackaged kits that could provide compositions required for performing such novel methods.

SUMMARY

Fluoride binds to practically all other elements and some of those bonds are relatively stable. Peptides, bearing metal binding ligands, are known to bind radiometals stably and at very high specific activity. The approach utilized in the present method was to first bind the F-18 to a metal and then chelate the F-18 metal complex with a ligand on the peptide. The question was then, which metal (or other element e.g. boron) to choose. The elements in group IIIA (boron, aluminum, gallium, indium, and thallium) were the first choice based on a quick search of the literature. Lutetium may also be of use.

Alternatively, one might attach the metal or other atom to the peptide first and then add the F-18. The second approach might work better, for example, for a boron fluoride connection.

Aluminum fluoride complexes are reported to be stable in-vitro (Martinez et al, *Inorg. Chem.* 1999; 38: 4765-4660;

Antonny et al. *J. Biol. Chem.* 1992; 267: 6710-6718). Aluminum fluoride becomes incorporated into bone and into the enamel of teeth so the complexes can also be stable in-vivo (Li, *Crit. Rev. Oral Biol. Med.* 2003; 14: 100-114).

The skilled artisan will realize that virtually any delivery molecule can be used to attach the F-18 for imaging purposes, so long as it contains derivatizable groups that may be modified without affecting the ligand-receptor binding interaction between the delivery molecule and the cellular or tissue target receptor. Although the Examples below concern F-18 labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, lipids, etc. may be F-18 labeled and utilized for imaging purposes. Similarly, the type of diseases or conditions that may be imaged is limited only by the availability of a suitable delivery molecule for targeting a cell or tissue associated with the disease or condition. Many such delivery molecules are known, as exemplified in the Examples below. For example, any protein or peptide that binds to a diseased tissue or target, such as cancer, may be labeled with F-18 by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with F-18 by the described methods and used for imaging and/or detection of tumors, for example by PET scanning or other known techniques.

In certain Examples below, the exemplary F-18 labeled peptides may be of use for imaging purposes as targetable constructs in a pre-targeting method, utilizing bispecific or multispecific antibodies or antibody fragments. In this case, the antibody or fragment will comprise one or more binding sites for a target associated with a disease or condition, such as a tumor-associated or autoimmune disease-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the entire contents of which are incorporated herein by reference.) Similarly, antibodies or fragments thereof that bind to targetable constructs are also well known in the art (Id.), such as the 679 monoclonal antibody that binds to HSG (histamine succinyl glycine). Generally, in pretargeting methods the bispecific or multispecific antibody is administered first and allowed to bind to cell or tissue target antigens. After an appropriate amount of time for unbound antibody to clear from circulation, the e.g. F-18 labeled targetable construct is administered to the patient and binds to the antibody localized to target cells or tissues, then an image is taken for example by PET scanning.

In an exemplary embodiment, a non-peptide receptor targeting agent such as folic acid may be conjugated to NOTA and then labeled with, for example, an F-18 metal complex that binds to NOTA. Such non-peptide receptor targeting agents may include, for example, TA138, a non-peptide antagonist for the integrin $\alpha_v\beta_3$ receptor (Liu et al., 2003, Bioconj. Chem. 14:1052-56). Similar non-peptide targeting agents known in the art that can be conjugated to DOTA, NOTA or another chelating agent for F-18 metal complexes may be utilized in the claimed methods. Other receptor targeting agents are known in the art, such as the somatostatin receptor targeting agent In-DTPA octreotide (TYCO®). As discussed below, an F-18-metal complex could potentially be chelated using DTPA and used for imaging purposes. The NODAGATOC peptide could be labeled with AlF-18 for somatostatin receptor targeting (Eisenwiener et. al. Bioconj. Chem. 2002, 13(3):530-41). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

Imaging techniques and apparatus for F-18 imaging by PET scanning are also well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

Although the Examples below demonstrate the use of F-18 metal complexes for PET imaging, the skilled artisan will realize that stable metal-fluorine complexes, such as the non-radioactive Al-27 and F-19 complex, could also be bound to NOTA or other chelators and attached to peptides or other targeting agents for use as an MRI contrast agent. The AlF NOTA complexes could also be attached to polymers for MRI imaging. The AlF NOTA derivatives could be used as PARACEST MRI imaging agents (Woessner et. al. Magn. Reson. Med. 2005, 53: 790-99).

BRIEF DESCRIPTION OF THE DRAWINGS

The following Figures are included to illustrate particular embodiments of the invention and are not meant to be limiting as to the scope of the claimed subject matter.

DETAILED DESCRIPTION

Figure 1:
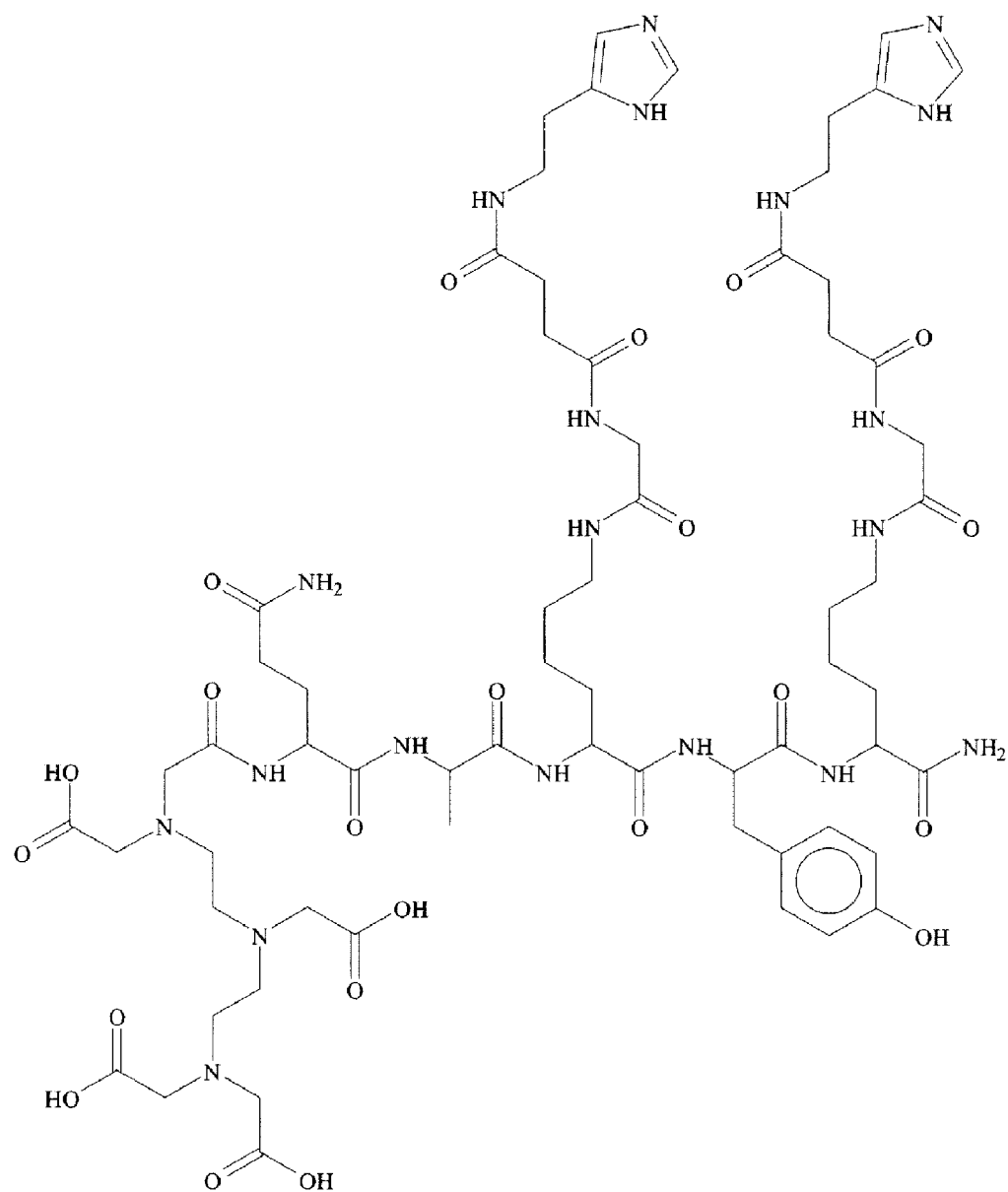
FIG. 1. Exemplary peptide IMP 272.

In the description that follows, a number of terms are used and the following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum,* Lyme disease spirochetes, *Pseudomonas aeruginosa, Mycobacterium leprae, Brucella abortus, Mycobacterium tuberculosis* and *Chlostridium tetani.*

As used herein, a "radiolysis protection agent" refers to any molecule, compound or composition that may be added to an F-18 labeled complex or molecule to decrease the rate of breakdown of the F-18 labeled complex or molecule by radiolysis. Any known radiolysis protection agent, including but not limited to ascorbic acid, may be used.

Targetable Construct Peptides

In certain embodiments, the F-18 labeled moiety may comprise a peptide or other targetable construct. F-18 labeled peptides (or proteins) may be selected to bind directly to a targeted cell, tissue, pathogenic organism or other target for imaging and/or detection. In other embodiments, F-18 labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as an F-18 labeled peptide, may be administered to the subject and allowed to bind to the bispecific antibody and localize to the diseased cell or tissue, after which the distribution of the F-18 labeled targetable construct may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. More usually, the targetable construct peptide will have four or more residues, such as the peptide DOTA-Phe-Lys(HSG)-Tyr-Lys(HSG)-NH$_2$ (SEQ ID NO: 1). wherein DOTA is 1,4,7,10-tetraazacyclododecanetetraacetic acid and HSG is the histamine succinyl glycyl group. Alternatively, the DOTA may be replaced by a NOTA (1,4,7-triaza-cyclononane-N,N', N"-triacetic acid) or TETA (p-bromoacetamido-benzyl-tetraethylaminetetraacetic acid) moiety.

The targetable construct may also comprise unnatural amino acids, e.g., D-amino acids, in the backbone structure to increase the stability of the peptide in vivo. In alternative embodiments, other backbone structures such as those constructed from non-natural amino acids and peptoids.

The peptides used as targetable constructs are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as a Boc group, while N-terminal residues may be acetylated to increase serum stability. Such protecting groups will be known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity.

The haptens of the immunogen comprise a recognition moiety, for example, a chemical hapten. Using a chemical hapten, preferably the HSG hapten, high specificity of the linker for the antibody is exhibited. Antibodies raised to the HSG hapten are known and can be easily incorporated into the appropriate bispecific antibody (see, e.g., U.S. Pat. Nos. 6,962,702; 7,138,103 and 7,300,644, the entire text of each of which is incorporated herein by reference). Thus, binding of the linker with the attached hapten would be highly specific for the antibody or antibody fragment.

Chelate Moieties

In some embodiments, an F-18 labeled molecule may comprise one or more hydrophilic chelate moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are also of use with a variety of metals, that may potentially be used as ligands for F-18 conjugation.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. Nos. 5,256,395) and are readily coupled to a targeting antibody to form a bispecific antibody, it is possible to use a peptide hapten with cold diDTPA chelator and another chelator for binding an F-18 complex, in a pretargeting protocol. One example of such a peptide is Ac-Lys(DTPA)-Tyr-Lys(DTPA)-Lys(Tscg-Cys)-NH$_2$ (SEQ ID NO:2). Other hard acid chelators such as DOTA, TETA and the like can be substituted for the DTPA and/or Tscg-Cys groups, and MAbs specific to them can be produced using analogous techniques to those used to generate the anti-di-DTPA MAb.

Another useful chelator may comprise a NOTA-type moiety, for example as disclosed in Chong et al. (Rational design and generation of a bimodal bifunctional ligand for antibody-targeted radiation cancer therapy, *J. Med. Chem.*, e-published on 12-7-07, incorporated herein by reference). Chong et al. disclose the production and use of a bifunctional C-NETA ligand, based upon the NOTA structure, that when complexed with $^{177}$Lu or $^{205/206}$Bi showed stability in serum for up to 14 days.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to F-18, to be incorporated into a targetable construct for eventual capture by a pretargeted bispecific antibody.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference in its entirety).

The administration of a bispecific antibody (bsAb) and an F-18 labeled targetable construct may be conducted by administering the bsAb antibody at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr (alternatively 48-96 hours) before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the F-18 labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

Alternatively, a technique known as "dock-and-lock" (DNL) has been demonstrated for the simple and reproducible construction of a variety of multivalent complexes, including complexes comprising two or more different antibodies or antibody fragments. (See, e.g., U.S. patent application Ser. Nos. 11/389,358, filed Mar. 24, 2006; 11/391,584, filed Mar. 28, 2006; 11/478,021, filed Jun. 29, 2006; 11/633,729, filed Dec. 5, 2006; and 11/925,408, filed Oct. 26, 2007, the text of each of which is incorporated herein by reference in its entirety.) Such constructs are also of use for the practice of the claimed methods and compositions described herein.

A clearing agent may be used which is given between doses of the bispecific antibody (bsAb) and the targetable construct. A clearing agent of novel mechanistic action may be used, namely a glycosylated anti-idiotypic Fab' fragment targeted against the disease targeting arm(s) of the bsAb. In one example, anti-CEA (MN-14 Ab)×anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the F-18 labeled targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety. However, alternative methods and compositions for clearing agents are known and any such known clearing agents may be used.

Formulation and Administration

The F-18 labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the F-18 labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parental injection. Injection may be intravenous, intraarterial, intralymphatic, intrathecal, or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising F-18 labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, for imaging purposes it is desirable to provide the recipient with a dosage of bispecific antibody hat is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject for imaging purposes are 1 to 200 mg, more preferably 1 to 70 mg, most preferably 1 to 20 mg, although higher or lower doses may be used.

In general, the dosage of F-18 label to administer will vary depending upon such factors as the patient's age, weight, height, sex, general medical condition and previous medical history. Preferably, a saturating dose of the F-18 labeled molecules is administered to a patient. For administration of F-18 labeled molecules, the dosage may be measured by millicuries. A typical range for F-18 imaging studies would be five to 10 mCi.

Administration of Peptides

Various embodiments of the claimed methods and/or compositions may concern one or more F-18 labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, F-18 labeled peptides are administered in a pretargeting protocol, the peptides would preferably be administered i.v.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based F-18 labeled molecules suitable for oral administration to a subject.

In certain embodiments, the standard peptide bond linkage may be replaced by one or more alternative linking groups, such as $CH_2—NH$, $CH_2—S$, $CH_2—CH_2$, $CH=CH$, $CO—CH_2$, $CHOH—CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act.

Endopeptidase binding and cleavage sequences are known in the art and methods for making and using peptides incorporating D-amino acids have been described (e.g., U.S. Patent Application Publication No. 20050025709, McBride et al., filed Jun. 14, 2004, incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

Methods for Raising Antibodies

Abs to peptide backbones may be generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the targetable construct, e.g., In(III)-DTPA chelates. Monoclonal mouse antibodies to an In(III)-di-DTPA are known (Barbet '395 supra).

Targeting antibodies of use, for example as components of bispecific antibodies, may be specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, each incorporated herein by reference. Recent reports on tumor associated antigens include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). Further it is known that TACI and B cell maturation antigen (BCMA) are bound by the tumor necrosis factor homolog—a proliferation-inducing ligand (APRIL). APRIL stimulates in vitro proliferation of primary B and T cells and increases spleen weight due to accumulation of B cells in vivo. APRIL also competes with TALL-I (also called BLyS or BATF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Exemplary target antigens of use for imaging various diseases or conditions, such as a malignant disease, a cardiovascular disease, an infectious disease, an inflammatory disease, an autoimmune disease, or a neurological disease may include colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD79a, CD80, HLA-DR, Ia, Ii, MUC 1, MUC 2, MUC 3, MUC 4, NCA (CEACAM6 or CD66a-d and CD67, as well as CD138), EGFR, HER 2/neu, TAG-72, EGP-1, EGP-2, A3, KS-1, Le(y), S100, PSMA, PSA, tenascin, folate receptor, VEGFR, PlGF, ILGF-1, necrosis antigens, IL-2, IL-6, T101, MAGE, or a combination of these antigens. In particular, antigens may include carcinoembryonic antigen (CEA), tenascin, epidermal growth factor receptor, platelet derived growth factor receptor, fibroblast growth factor receptors, vascular endothelial growth factor receptors, gangliosides, HER/2neu receptors and combinations of these antigens.

Where imaging or detection involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, 11, HM1.24, HLA-DR, tenascin, VEGF, PlGF, ED-B fibronectin, an oncogene, an oncogene product, CD66a-d, necrosis antigens, IL-2, T101, TAG, IL-6, MIF, TRAIL-R1 (DR4) and TRAIL-R2 (DR5).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is incorporated herein by reference in its entirety.

Alternatively, fully human antibodies can be obtained from transgenic non-human animals. See, e.g., Mendez et al., Nature Genetics, 15: 146-156 (1997); U.S. Pat. No. 5,633, 425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment may be derived from human antibody fragments isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994), which are incorporated herein by reference. Many of the difficulties associated with generating monoclonal antibodies by B-cell immortalization can be overcome by engineering and expressing antibody fragments in $E.\ coli$, using phage display.

A similar strategy can be employed to obtain high-affinity scFv. See, e.g., Vaughn et al., Nat. Biotechnol., 14: 309-314 (1996). An scFv library with a large repertoire can be constructed by isolating V-genes from non-immunized human donors using PCR primers corresponding to all known $V_H$, $V_{kappa}$ and $V_{80}$ gene families. Following amplification, the $V_{kappa}$ and $V_{lambda}$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (NUNC®; MAXISORP®). Similar results can be achieved by constructing a combinatorial immunoglobulin library from lymphocytes or spleen cells of immunized rabbits and by expressing the scFv constructs in $P.\ pastoris$. See, e.g., Ridder et al., Biotechnology, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181-188 (1998); Osbourn et al., Immunotechnology, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Bispecific antibodies can be prepared by techniques known in the art, for example, an anti-CEA tumor Ab and an anti-peptide Ab are both separately digested with pepsin to their respective F(ab')$_2$ fragments. The anti-CEA-Ab-F(ab')$_2$ is reduced with cysteine to generate Fab' monomeric units which are further reacted with the cross-linker bis(maleimido) hexane to produce Fab'-maleimide moieties. The anti-peptide Ab-F(ab')$_2$ is reduced with cysteine and the purified, recovered anti-peptide Fab'-SH is reacted with the anti-CEA-Fab'-maleimide to generate the Fab'×Fab' bi-specific Ab. Alternatively, the anti-peptide Fab'-SH fragment may be coupled with the anti-CEA F(ab')$_2$ to generate a F(ab')$_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bispecific antibodies include engineered recombinant Abs which have additional cysteine residues so that they crosslink more strongly than the more common immunoglobulin isotypes. See, e.g., FitzGerald et al., Protein Eng. 10:1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021-7025, 1995.

Preferred bispecific antibodies are those which incorporate the Fv of MAb Mu-9 and the Fv of MAb 679 or the Fv of MAb MN-14 and the Fv of MAb 679, and their human, chimerized or humanized counterparts. The MN-14, as well as its chimerized and humanized counterparts, are disclosed in U.S. Pat. No. 5,874,540. Also preferred are bispecific antibodies which incorporate one or more of the CDRs of Mu-9 or 679. The antibody can also be a fusion protein or a bispecific antibody that incorporates a Class III anti-CEA antibody and the Fv of 679. Class III antibodies, including Class III anti-CEA are discussed in detail in U.S. Pat. No. 4,818,709.

The skilled artisan will realize that bispecific antibodies may incorporate any antibody or fragment known in the art that has binding specificity for a target antigen that is known to be associated with a disease state or condition. Such known antibodies include, but are not limited to, LL1 (anti-CD74), LL2 and RFB4 (anti-CD22), hA20 (anti-CD20), RS7 (anti-epithelial glycoprotein-1 (EGP-1)), PAM-4 and KC4 (both anti-mucin), MN-14 (anti-carcinoembryonic antigen (CEA, also known as CD66e)), MN-3 or MN-15 (NCA or CEACAM6), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX MAb) and L243 (anti-HLA-DR). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; and U.S. Patent Application Publ. No. 20040185053; 20040202666; 20050271671; 20060193865; 20060210475; 20070087001; each incorporated herein by reference in its entirety.) Such known antibodies are of use for detection and/or imaging of a variety of disease states or conditions (e.g., hMN-14 or 11-2 bsMAb (CEA-expressing carcinomas), hA20 bsMab (TF-4-lymphoma), hPAM4 (TF-10 pancreas cancers), RS7 bsMAb (lung, breast, ovarian, prostatic cancers), hMN-15 or hMN3 bsMAb (inflammation), human gp120 and/or gp41 bsMAbs (HIV), anti-platelet bsMab and anti-thrombin bsMAb (clot imaging), anti-myosin bsMAb (cardiac necrosis)).

Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agens Chemother. 2006; 50(5):1773-9, all incorporated herein in their entirety by reference.

In certain embodiments, the bsAb F-18 labeled targetable constructs discussed above may be used in intraoperative, intravascular, and/or endoscopic tumor and lesion detection, biopsy and therapy as described in U.S. Pat. No. 6,096,289.

Imaging Using Labeled Molecules

Methods of imaging using labeled molecules are well known in the art, and any such known methods may be used with the fluoride-labeled molecules disclosed herein. See, e.g., U.S. Pat. Nos. 6,241,964; 6,358,489; 6,953,567 and published U.S. Patent Application Publ. Nos. 20050003403; 20040018557; 20060140936, each incorporated herein by reference in its entirety. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

In certain embodiments, F-18 labeled molecules may be of use in imaging normal or diseased tissue and organs, for example using the methods described in U.S. Pat. Nos. 6,126, 916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001. Such imaging can be conducted by direct F-18 labeling of the appropriate targeting molecules, or by a pretargeted imaging method, as described in Goldenberg et al. (2007, Update Cancer Ther. 2:19-31); Sharkey et al. (2008, Radiology 246: 497-507); Goldenberg et al. (2008, J. Nucl. Med. 49:158-63); Sharkey et al. (2007, Clin. Cancer Res. 13:5777s-5585s); McBride et al. (2006, J. Nucl. Med. 47:1678-88); Goldenberg et al. (2006, J. Clin. Oncol. 24:823-85), see also U.S. Patent Publication Nos. 20050002945, 20040018557, 20030148409 and 20050014207, each incorporated herein by reference.

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBOD- IES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such radionuclides may be imaged by well-known PET scanning techniques.

EXAMPLES

Example 1

F-18 Labeling of Peptide IMP 272

The first peptide that was used was IMP 272:
DTPA-Gln-Ala-Lys(HSG)-D-Tyr-Lys(HSG)-NH$_2$ MH$^+$ 1512

Acetate buffer solution—Acetic acid, 1.509 g was diluted in ~160 mL water and the pH was adjusted by the addition of 1 M NaOH then diluted to 250 mL to afford a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28×10$^{-7}$ mol IMP 272 was dissolved in 364 µL of the 0.1 M pH 4 acetate buffer solution to obtain a 2 mM stock solution of the peptide.

F-18 Labeling of IMP 272—A 3 µL aliquot of the aluminum stock solution was placed in a REACTI-VIAL™ and mixed with 50 µL F-18 (as received) and 3 µL of the IMP 272 solution. The solution was heated in a heating block at 110° C. for 15 min and analyzed by reverse phase HPLC. The HPLC trace (not shown) showed 93% free F-18 and 7% bound to the peptide. An additional 10 µL of the IMP 272 solution was added to the reaction and it was heated again and analyzed by reverse phase HPLC (not shown). The HPLC trace showed 8% F-18 at the void volume and 92% of the activity attached to the peptide. The remainder of the peptide solution was incubated at room temperature with 150 µL PBS for ~1 hr and then examined by reverse phase HPLC. The HPLC (not shown) showed 58% F-18 unbound and 42% still attached to the peptide. The data indicate that F-18-Al-DTPA complex may be unstable when mixed with phosphate.

Reverse Phase HPLC—Reverse phase HPLC analysis was done under the following conditions:
Column: WATERS® XTERRA™ MS C$_{18}$ 5 µm, 4.6×250 mm
Flow Rate: 1 mL/min
Gradient Buffers Buffer C, 0.1% NH$_4$OAc in DI water, Buffer D, 90% acetonitrile 10% water and 0.1% NH$_4$OAc
Gradient: 100% Buffer C to 100% Buffer D using a linear gradient over 30 min.
Run Time: 30 min Size Exclusion HPLC—The size exclusion HPLC was done under the following conditions:
Column: BIORAD® BIO-SIL™ SEC 250, 300×7.8 mm
Gradient: Isocratic
Eluent Buffer: 0.2 M Phosphate pH 6.8
Flow Rate: 1 mL/min
Run Time: 30 min All radiometric traces were obtained using a PERKIN ELMER® 610Tr to monitor the emission of F-18. Tables 1-3 are tabular representations of the data.

TABLE 1

F-18 + IMP 272 + AlCl$_3$ heated at 110° C. for 15 min, followed by analysis by reverse phase HPLC.
Regions: F-18
Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 130.0 | | | |
| Region 1 | 2.30 | 3.30 | 2.60 | 85270.0 | 200050.0 | 93.15 | 96.31 |
| Bkg 2 | 4.40 | 4.50 | 4.40 | 210.0 | | | |
| Region 2 | 8.70 | 9.80 | 9.00 | 5590.0 | 14720.0 | 6.85 | 7.09 |
| 2 Peaks | | | | | 214770.0 | 100.00 | 103.40 |

TABLE 2

F-18 + excess IMP 272 + AlCl$_3$ heated at 110° C. for 15 min, followed by analysis by reverse phase HPLC.
Regions: F-18
Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 340.0 | | | |
| Region 1 | 2.40 | 3.20 | 2.70 | 6450.0 | 20549.6 | 7.76 | 8.23 |
| Bkg 2 | 7.10 | 7.20 | 7.10 | 630.0 | | | |
| Region 2 | 7.30 | 8.70 | 8.50 | 3140.0 | 13113.6 | 4.95 | 5.25 |
| Region 3 | 8.70 | 10.00 | 9.00 | 93700.0 | 231023.9 | 87.28 | 92.57 |
| Bkg 3 | 10.70 | 10.80 | 10.70 | 520.0 | | | |
| 3 Peaks | | | | | 264687.1 | 100.00 | 106.06 |

TABLE 3

Phosphate Challenge in PBS for 90 min at room temp. Aliquot of F-18 + excess IMP 272 + AlCl₃ heated at 110° C. for 15 min and analyzed by reverse phase HPLC.
Regions: F-18
Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.00 | 2.10 | 2.00 | 350.0 | | | |
| Region 1 | 2.40 | 3.30 | 2.70 | 81930.0 | 162403.6 | 58.23 | 62.44 |
| Bkg 2 | 4.20 | 4.30 | 4.20 | 410.0 | | | |
| Bkg 3 | 7.50 | 7.60 | 7.50 | 780.0 | | | |
| Region 2 | 7.80 | 8.60 | 8.40 | 2110.0 | 5564.7 | 2.00 | 2.14 |
| Region 3 | 8.60 | 9.80 | 8.90 | 44590.0 | 110942.0 | 39.78 | 42.66 |
| Bkg 4 | 10.50 | 10.60 | 10.50 | 460.0 | | | |
| 3 Peaks | | | | | 278910.3 | 100.00 | 107.24 |

The labeled peptide was purified by applying the labeled peptide solution onto a 1 cc (30 mg) WATERS® HLB column (Part #186001879) and washing with 300 µL water to remove unbound F-18. The peptide was eluted by washing the column with 2×100 µL 1:1 MeOH/H$_2$O. The purified peptide was incubated in water at 25° C. and analyzed by reverse phase HPLC (not shown). The HPLC analysis showed that the F-18 labeled IMP 272 was not stable in water. After 40 min incubation in water about 17% of the F-18 was released from the peptide, while 83% was retained (not shown).

Example 2

Immunoreactivity of F-18 IMP 272

The peptide (16 µL 2 mM IMP 272, 48 µg) was labeled with F-18 and analyzed for antibody binding by size exclusion HPLC. The size exclusion HPLC showed that the peptide bound hMN-14×679 but did not bind to the irrelevant bispecific antibody hMN-14×734 (not shown).

Example 3

IMP 272 F-18 Labeling with Other Metals

A ~3 µL aliquot of the metal stock solution (6×10⁻⁹ mol) was placed in a polypropylene cone vial and mixed with 75 µL F-18 (as received), incubated at room temperature for ~2 min and then mixed with 20 µL of a 2 mM (4×10⁻⁸ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown).

Example 4

Standard F-18 Peptide Labeling Conditions Used to Screen Other Peptides For Al-¹⁸F Binding A 3 µL aliquot of the 2 mM aluminum stock solution was placed in a polypropylene cone vial and mixed with 50 µL F-18 (as received), incubated at room temperature for ~2 min and then mixed with 16 to 20 µL of a 2 mM peptide solution in 0.1 M NaOAc pH 4 buffer. The solution was heated in a heating block at 100° C. for 15 min and analyzed by reverse phase HPLC (PHENOMENEX™, GEMINI®, 5µ, C-18, 110A, 250×4.6 mm HPLC Column).

Peptides Tested

IMP 272: DTPA-Gln-Ala-Lys(HSG)-D-Tyr-Lys(HSG)-NH$_2$ MH⁺ 1512 (FIG. 1)

Figure 2:
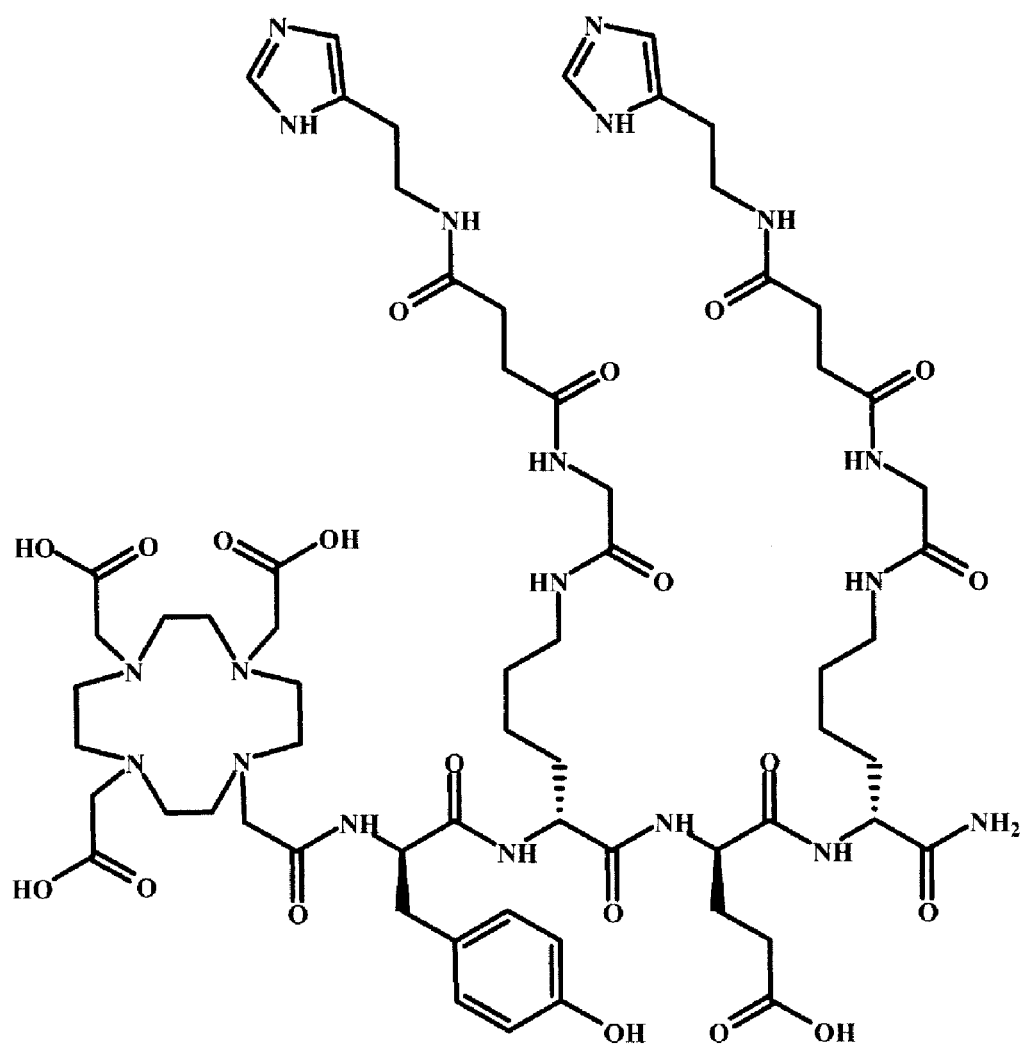
FIG. 2. Exemplary peptide IMP 288.

IMP 288 DOTA-D-Tyr-D-Lys(HSG)-D-Glu-D-Lys(HSG)-NH$_2$ MH⁺ 1453 (FIG. 2)

Figure 3:
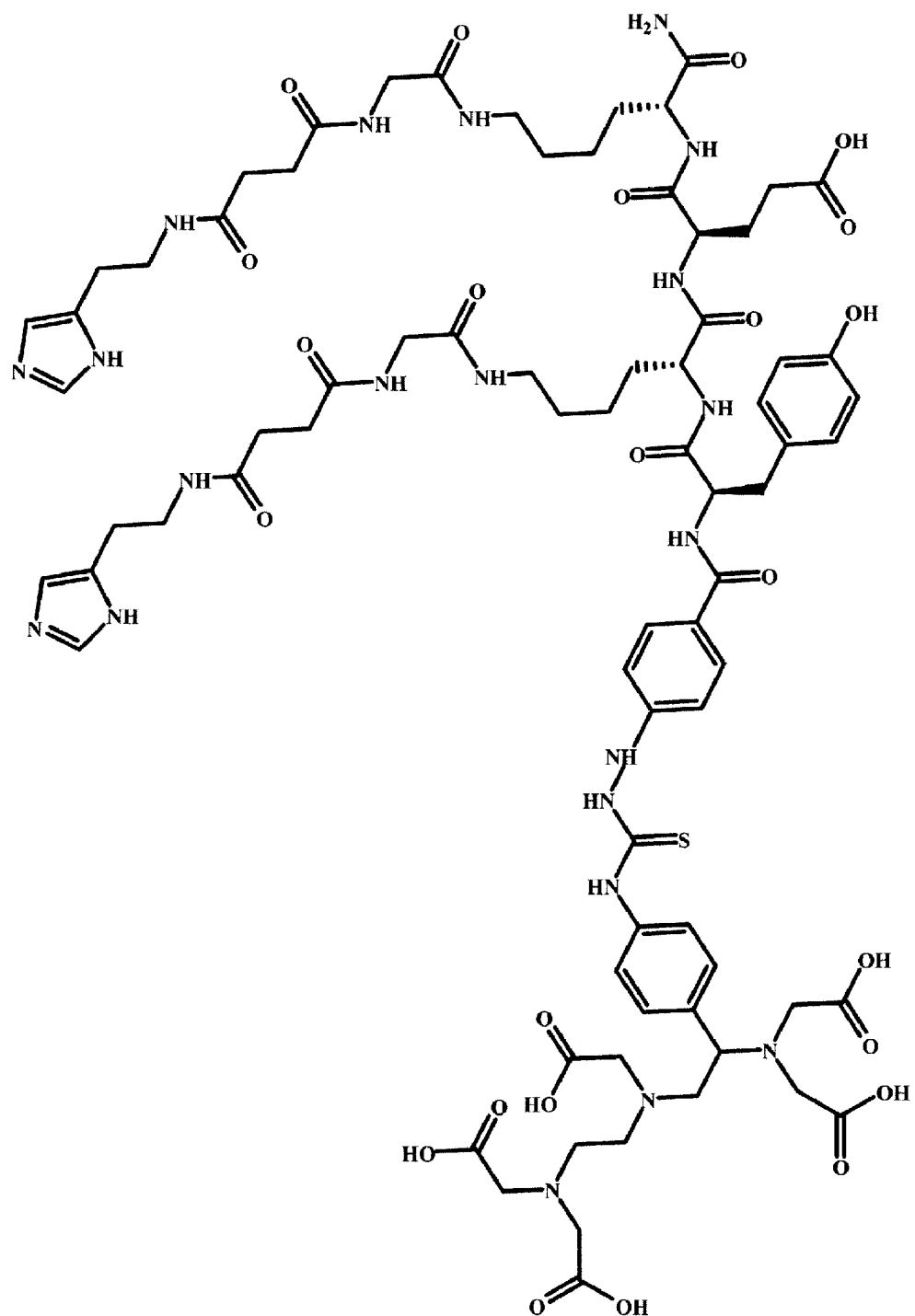
FIG. 3. Exemplary peptide IMP 326.

IMP 326 DTPA-ITC-NH—NH-Phe-CO-D-Tyr-D-Lys(HSG)-D-Glu-D-Lys(HSG)-NH$_2$ MH⁺ 1477 (FIG. 3)

Figure 4:
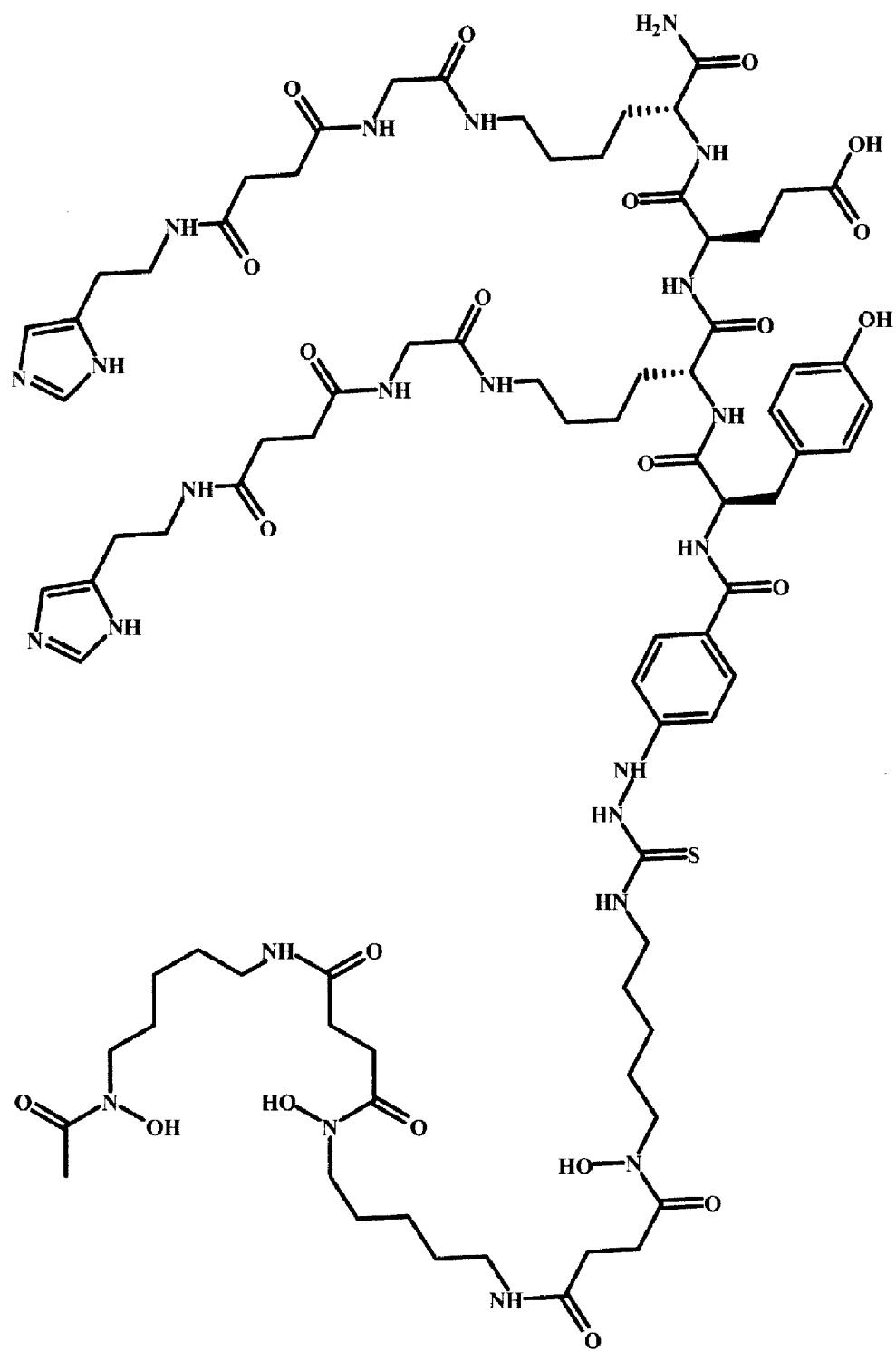
FIG. 4. Exemplary peptide IMP 329.

IMP 329 Deferoxamine-NH—CS—NH—NH-Ph-CO-D-Tyr-D-Lys(HSG)-D-Glu-D-Lys(HSG)-NH$_2$ MH⁺ 1804 (FIG. 4)

Figure 5:
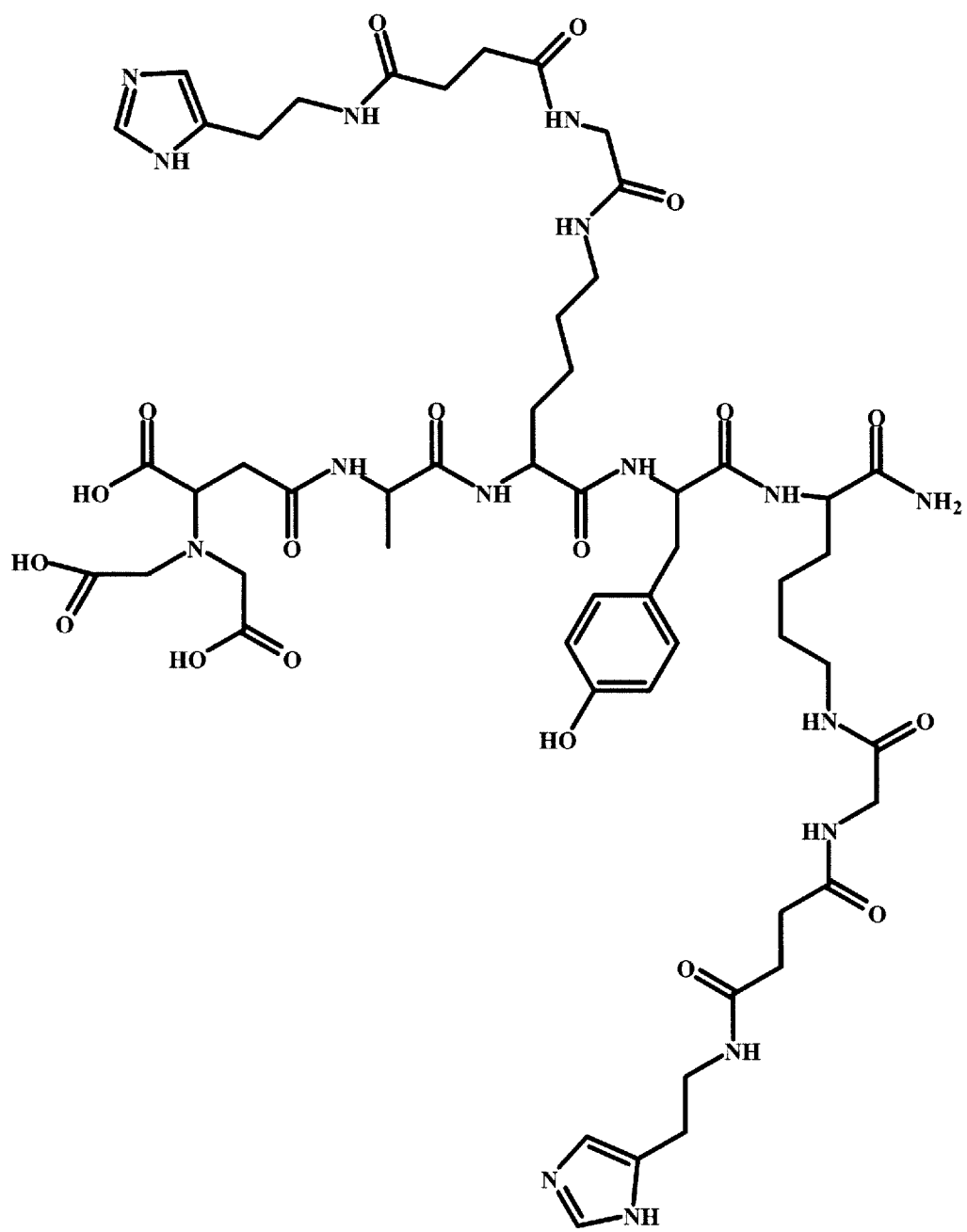
FIG. 5. Exemplary peptide IMP 331.

IMP 331 NTA-iAsp-D-Ala-D-Lys(HSG)-D-Tyr-D-Lys(HSG)-NH$_2$ MH⁺ 1240 (FIG. 5)

Figure 6:
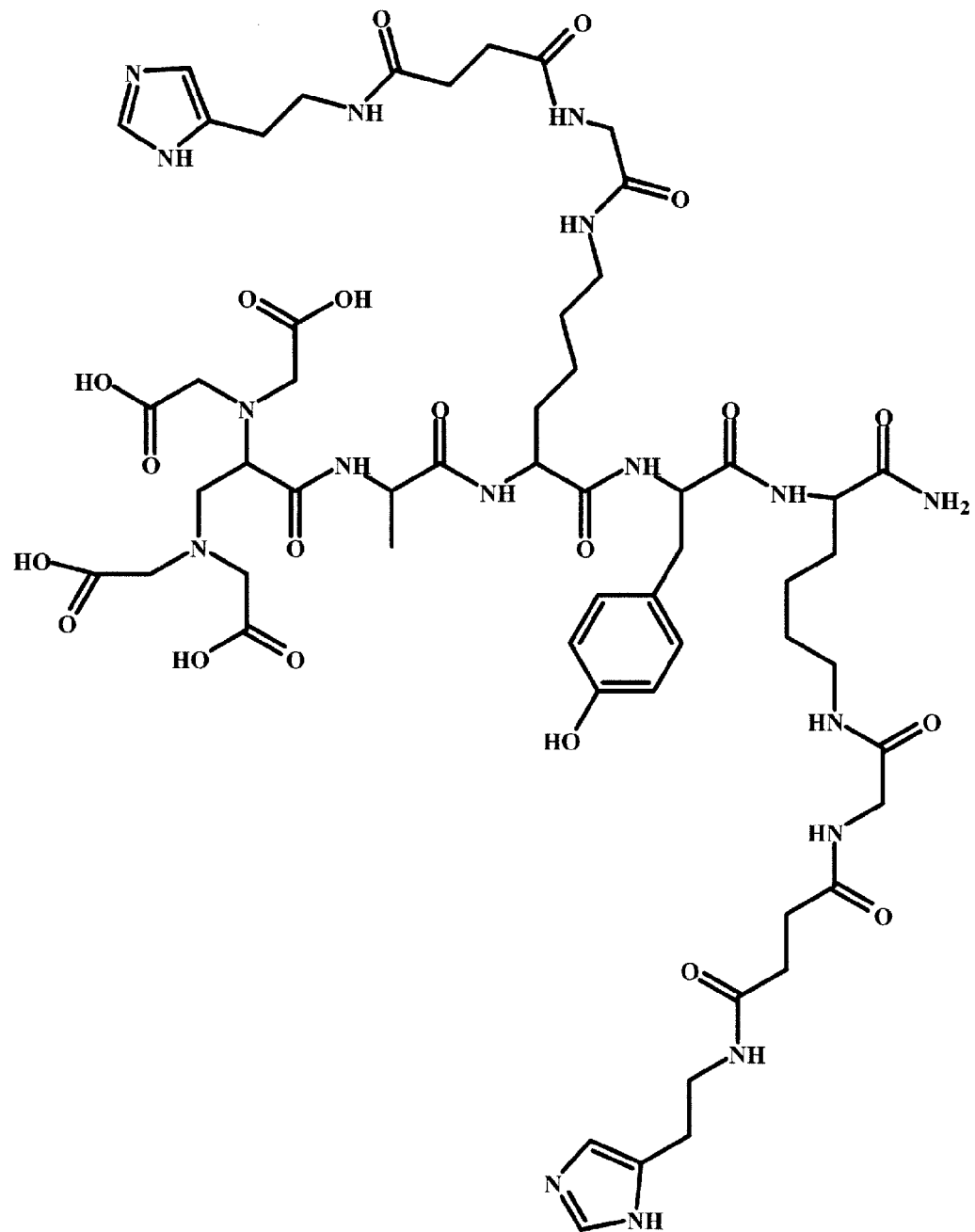
FIG. 6. Exemplary peptide IMP 332.

IMP 332 EDTADpr-D-Ala-D-Lys(HSG)-D-Ala-D-Lsy(HSG)-NH$_2$ MH⁺ 1327 (FIG. 6)

Figure 7:
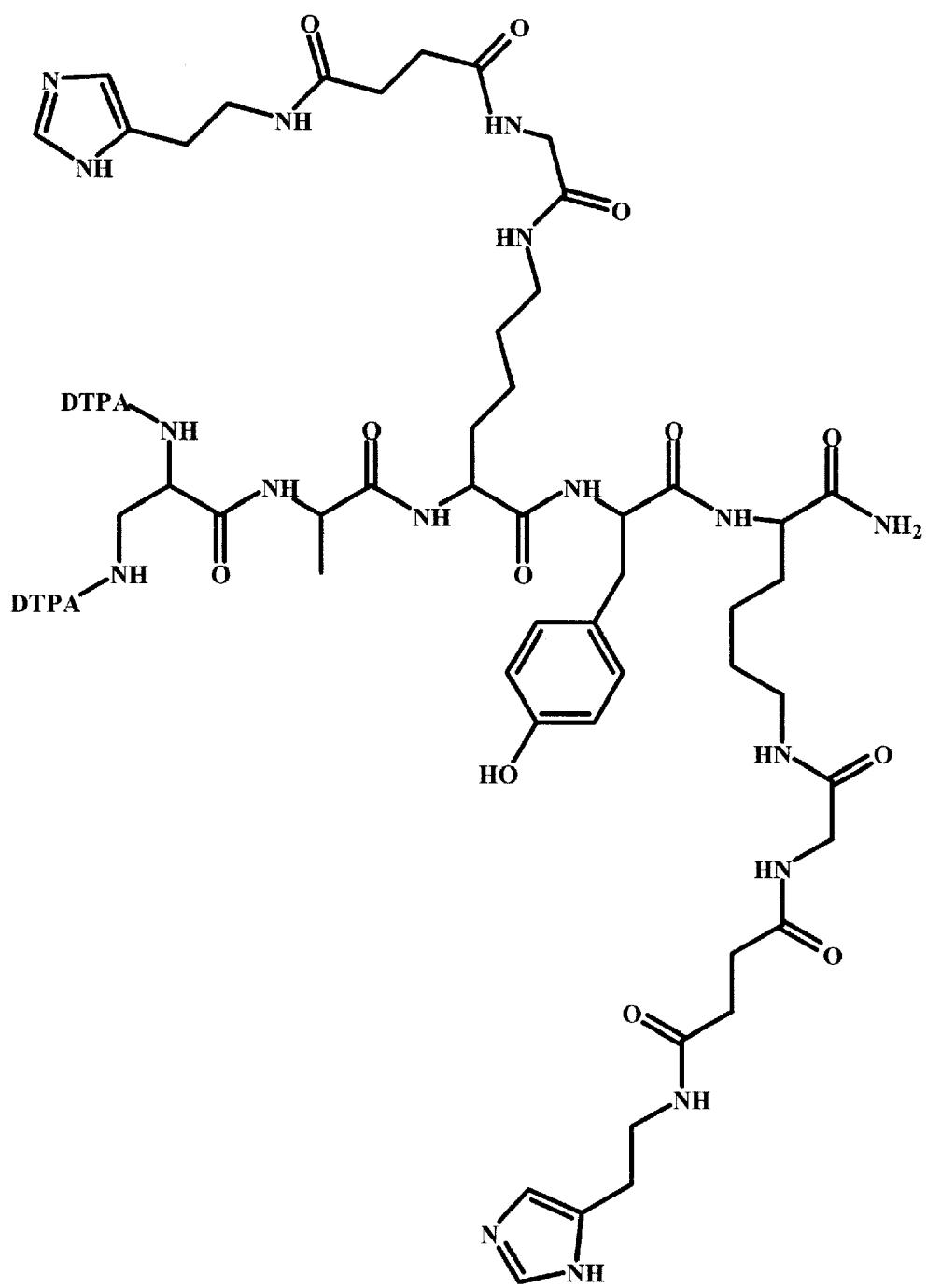
FIG. 7. Exemplary peptide IMP 333.

IMP 333 DTPA-Dpr(DTPA)-D-Ala-D-Lys(HSG)-D-Ala-D-Lys(HSG)-NH$_2$ MH⁺ 1845 (FIG. 7)

Figure 8:
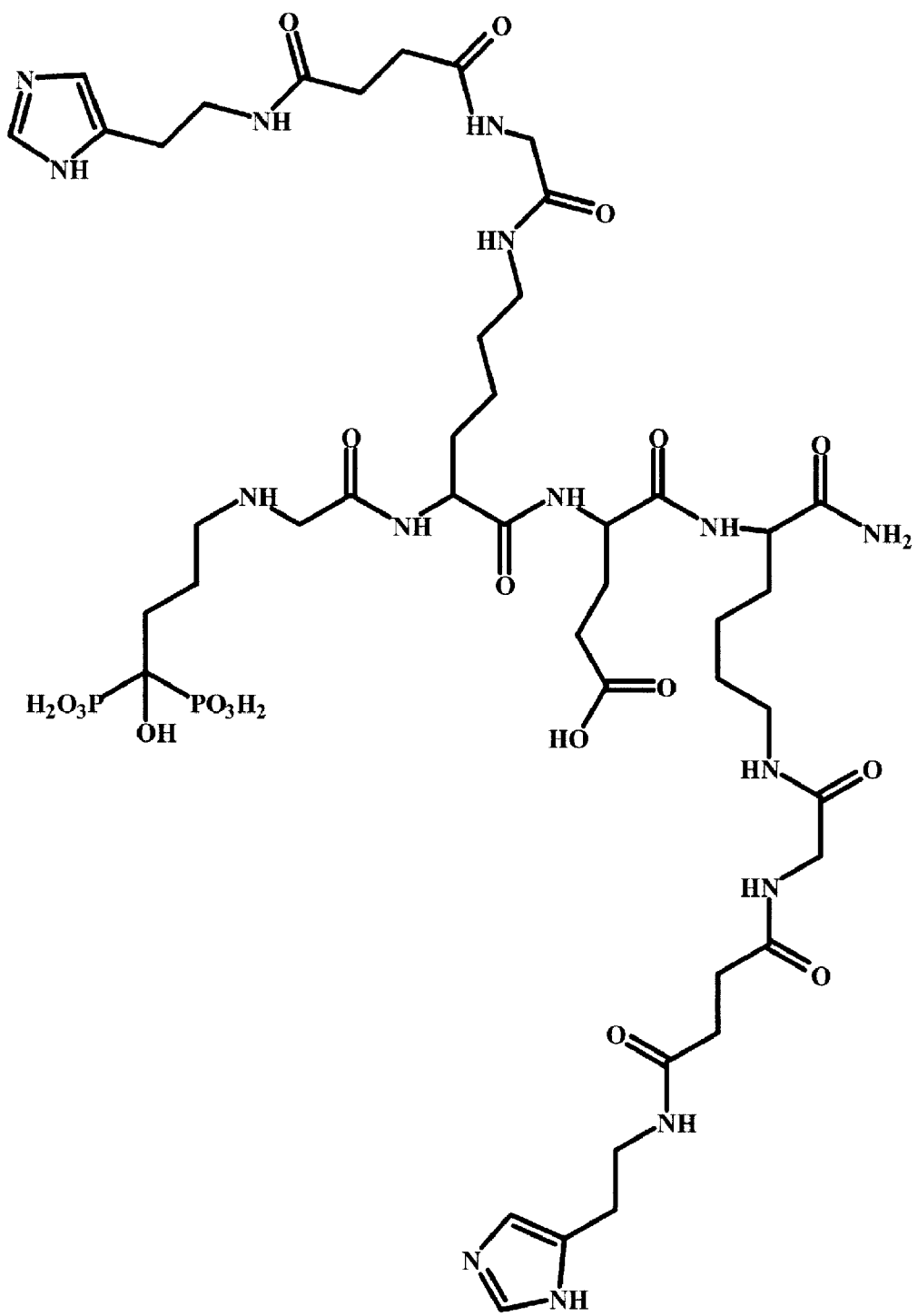
FIG. 8. Exemplary peptide IMP 334.

IMP 334 (H$_2$O$_3$P)$_2$—C(OH)—(CH2)$_3$—NH-Gly-D-Lys(HSG)-D-Glu-D-Lys(HSG)-NH$_2$ MH⁺ 1192 (FIG. 8)

IMP 337 Ac-D-Ser(PO$_3$H$_2$)-D-Ser(PO$_3$H$_2$)-D-Ala-D-Lys(HSG)-D-Ala-D-Lys(HSG)-NH$_2$ MH⁺ 1291

IMP 338 Ac-D-Ser(PO$_3$H$_2$)-D-Ala-D-Lys(HSG)-D-Ala-D-Lys(HSG)-NH$_2$ MH⁺ 1126

IMP 345 DTPA-D-Ser(PO$_3$H$_2$)-D-Ala-D-Lys(HSG)-D-Ala-D-Lys(HSG)-NH$_2$ MH⁺ 1459

Figure 9:
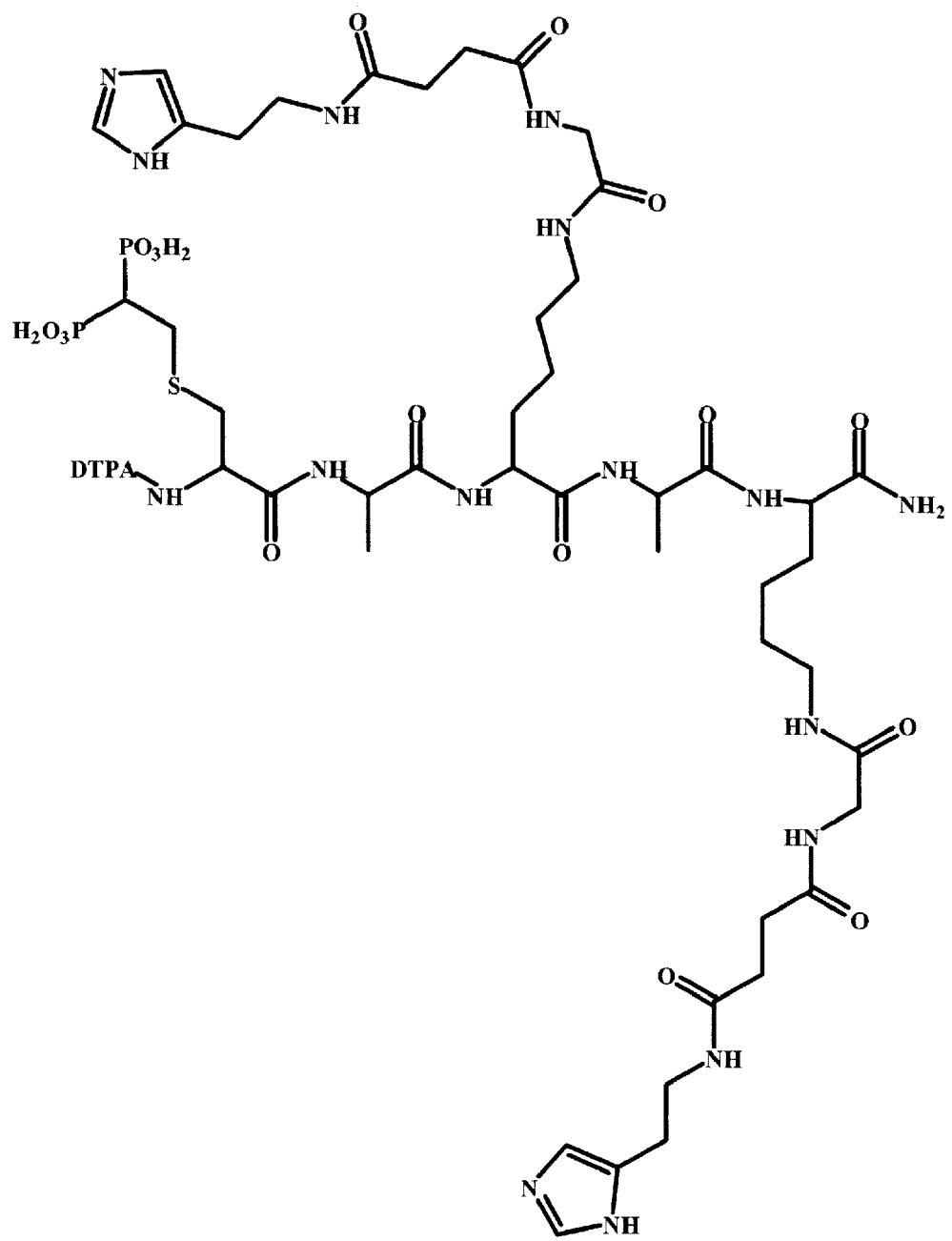
FIG. 9. Exemplary peptide IMP 349.

IMP 349 DTPA-D-Cys((H$_2$O$_3$P)$_2$—CH—CH$_2$—S)-D-Ala-D-Lys(HSG)-D-Ala-D-Lys(HSG)-NH$_2$ MH⁺ 1583 (FIG. 9)

IMP 361 DTPA-Dpr(BrCH$_2$CO—)-D-Ala-D-Lys(HSG)-D-Ala-D-Lys(HSG)-NH$_2$ MH⁺ 1498

IMP 366 DTPA-Dpr(Ph-S—CH$_2$CO—)-D-Ala-D-Lys(HSG)-D-Ala-D-Lys(HSG)-NH$_2$ MH⁺ 1528

Figure 10:
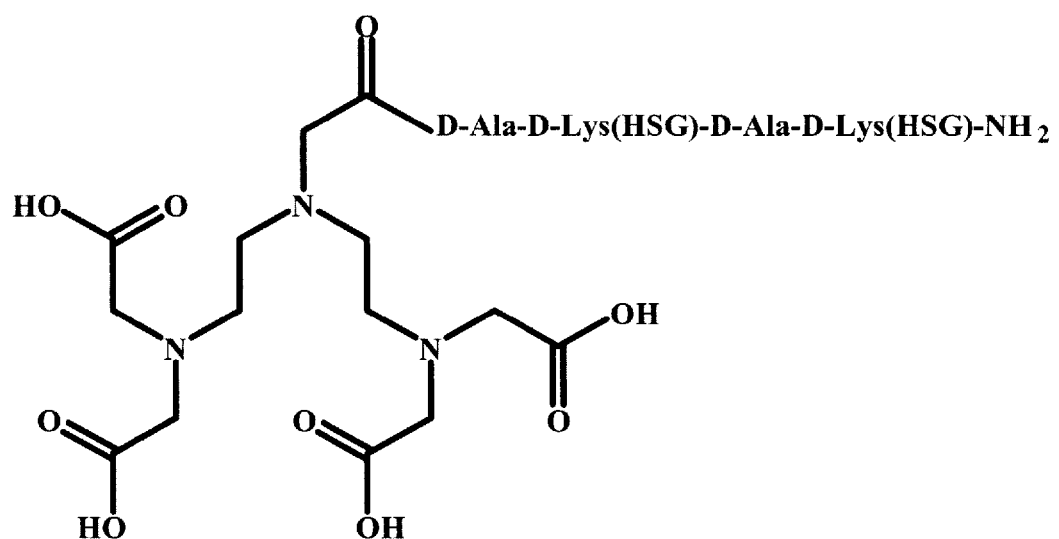
FIG. 10. Exemplary peptide IMP 368.

IMP 368 Sym-DTPA-D-Ala-D-Lys(HSG)-D-Ala-D-Lys(HSG)-NH$_2$ MH⁺ 1292 (FIG. 10)

IMP 369 Sym-DTPA-NH—CH(2-Br-Phe-)—CH$_2$—CO— D-Ala-D-Lys(HSG)-D-Ala-D-Lys(HSG)-NH$_2$ MH⁺ 1517

IMP 370 Sym-DTPA-NH—CH(2-O$_2$N-Phe-)—CH$_2$—CO— D-Ala-D-Lys(HSG)-D-Ala-D-Lys(HSG)-NH$_2$ MH⁺ 1484

IMP 371 DTPA-NH—CH(2-O$_2$N-Phe-)—CH$_2$—CO—D-Ala-D-Lys(HSG)-D-Ala-D-Lys(HSG)-NH$_2$ MH⁺ 1484

IMP 372 DTPA-Dpr(Ser)-D-Ala-D-Lys(HSG)-D-Ala-D-Lys(HSG)-NH$_2$ 1465

IMP 373 DTPA-Dpr(Sym-DTPA)-D-Ala-D-Lys(HSG)-D-Ala-D-Lys(HSG)-NH$_2$ MH⁺ 1753

IMP 374 DTPA-Dpr(Cl—CH2CO-Cys(Et)-)-D-Ala-D-Lys(HSG)-D-Ala-D-Lys(HSG)-NH$_2$ MH⁺ 1585

Figure 11:
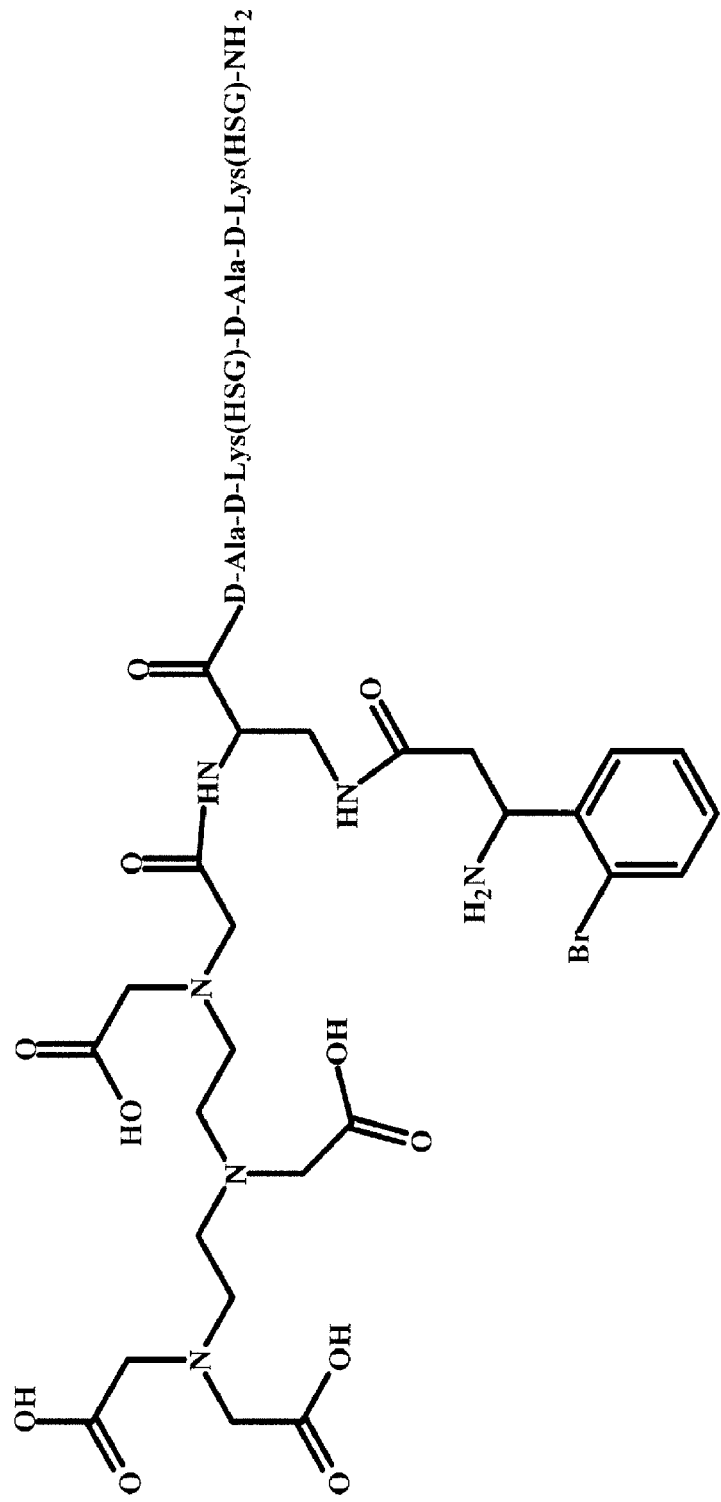
FIG. 11. Exemplary peptide IMP 375.

IMP 375 DTPA-Dpr(2-Br-Phe-CHNH$_2$—CH$_2$—CO—)-D-Ala-D-Lys(HSG)-D-Ala-D-Lys(HSG)-NH$_2$ MH$^+$ 1603 (FIG. 11)

IMP 376 DTPA-Cys(HO$_3$S—S)-D-Tyr-D-Ala-D-Lys(HSG)-D-Ala-D-Lys(HSG)-NH$_2$ MH$^+$ 1558

IMP 379 DTPA-Dpr(2-H$_2$N-Phe-CO—)-D-Ala-D-Lys(HSG)-D-Ala-D-Lys(HSG)-NH$_2$ MH$^+$ 1497

IMP 382 DTPA-Dpr(H)-D-Ala-D-Lys(HSG)-D-Ala-D-Lys(HSG)-NH$_2$ MH$^+$ 1378

IMP 383 DTPA-Dpr(Gla-)-D-Ala-D-Lys(HSG)-D-Ala-D-Lys(HSG)-NH$_2$ MH$^+$ 1507

Figure 12:
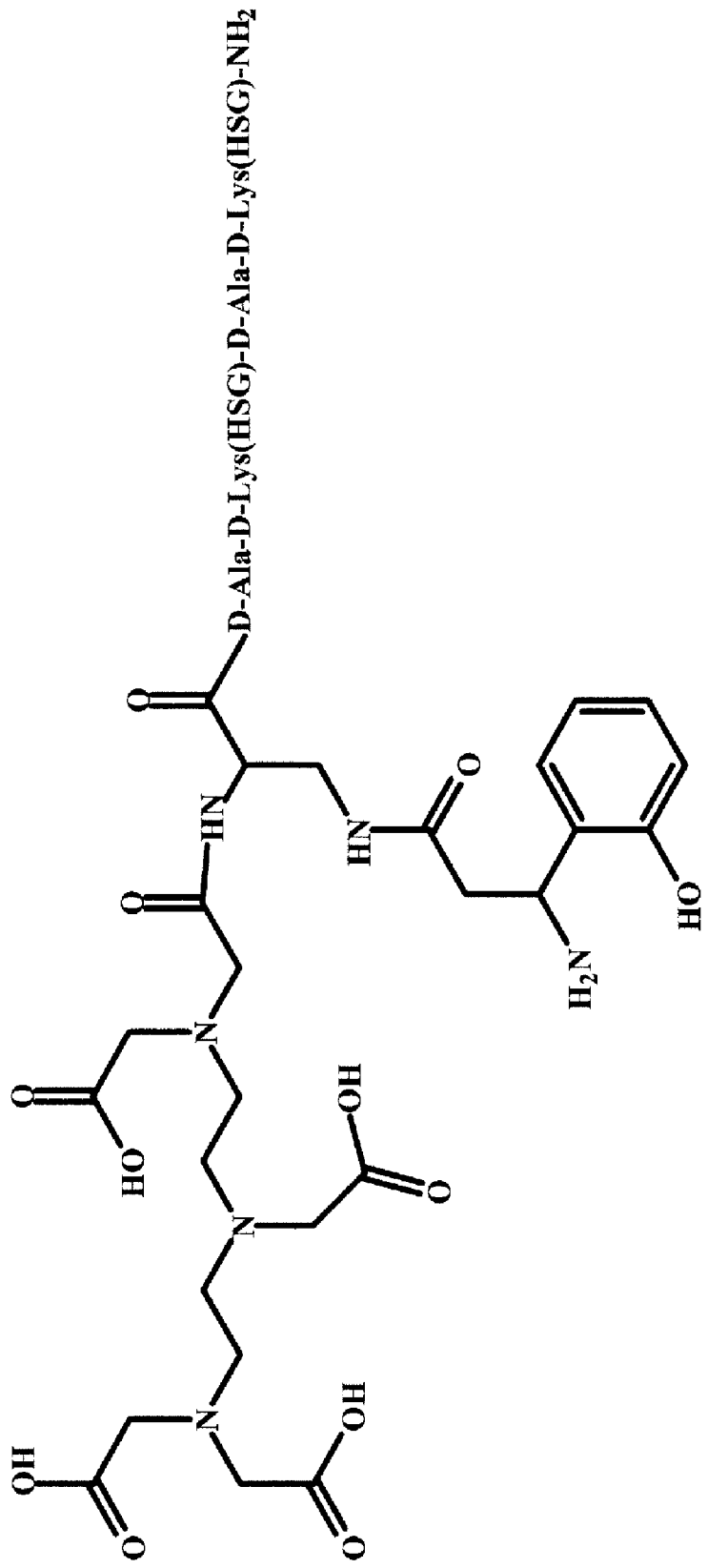
FIG. 12. Exemplary peptide IMP 384.

IMP 384 DTPA-Dpr(2-HO-Phe-CHNH$_2$—CH$_2$—CO—)-D-Ala-D-Lys(HSG)-D-Ala-D-Lys(HSG)-NH$_2$ MH$^+$ 1541 (FIG. 12)

IMP 385 DTPA-Dpr(Dpr)-D-Ala-D-Lys(HSG)-D-Ala-D-Lys(HSG)-NH$_2$ MH$^+$ 1464

Figure 13:
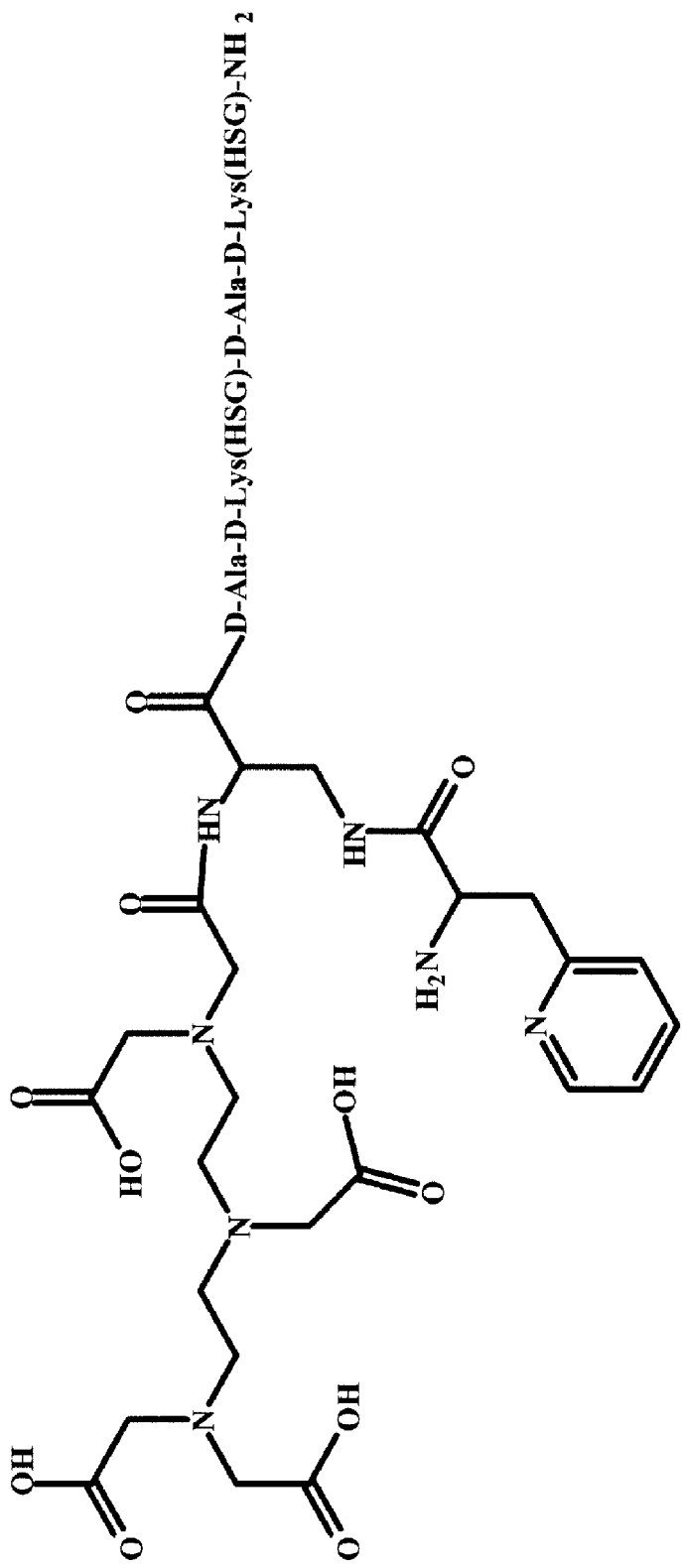
FIG. 13. Exemplary peptide IMP 386.

IMP 386 DTPA-Dpr(2-pyridyl-CH$_2$—CHNH$_2$—CO—)-D-Ala-D-Lys(HSG)-D-Ala-D-Lys(HSG)-NH$_2$ MH$^+$ 1526 (FIG. 13)

IMP 387 DTPA-Dpr(D-9-anthrylalanine)-D-Ala-D-Lys(HSG)-D-Ala-D-Lys(HSG)-NH$_2$ MH$^+$ 1625

Figure 14:
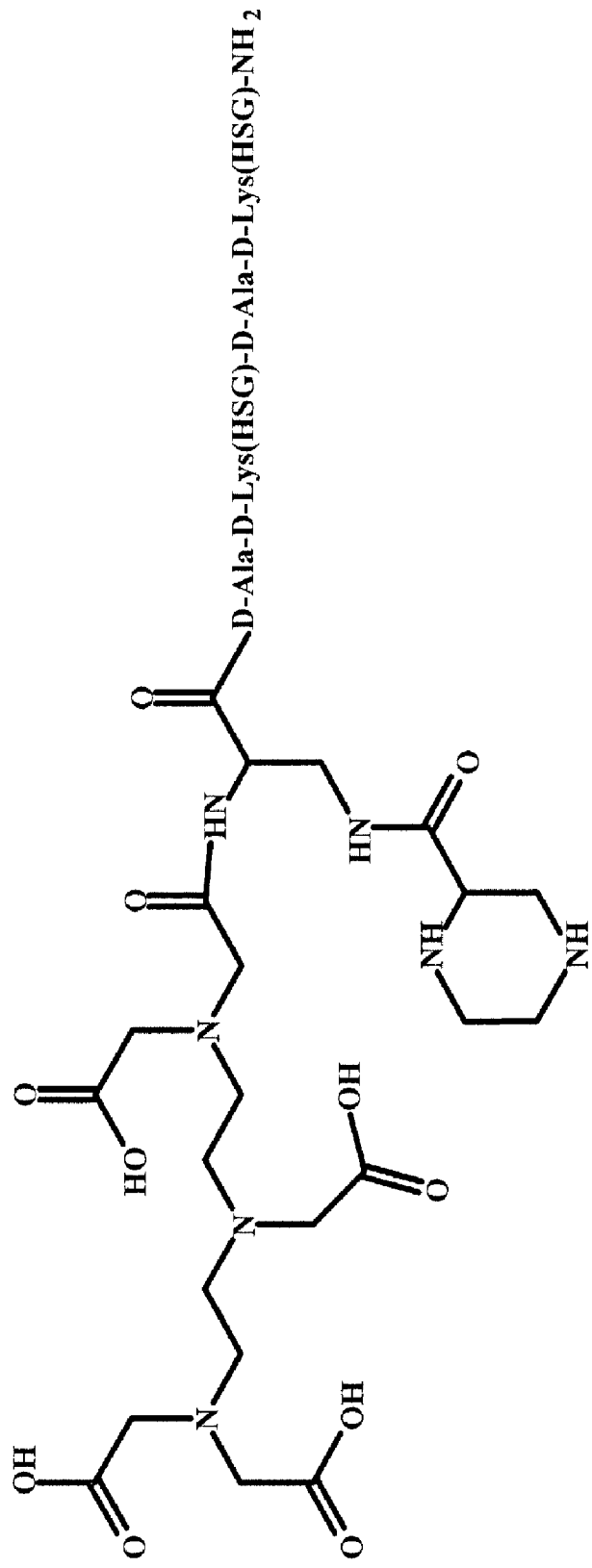
FIG. 14. Exemplary peptide IMP 389.

IMP 389 DTPA-Dpr(2-carboxy piperizinyl)-D-Ala-D-Lys(HSG)-D-Ala-D-Lys(HSG)—NH$_2$ MH$^+$ 1490 (FIG. 14)

IMP 460 NODA-GA-D-Ala-D-Lys(HSG)-D-Tyr-D-Lys(HSG)-NH2 MH$^+$ 1366

Figure 15:
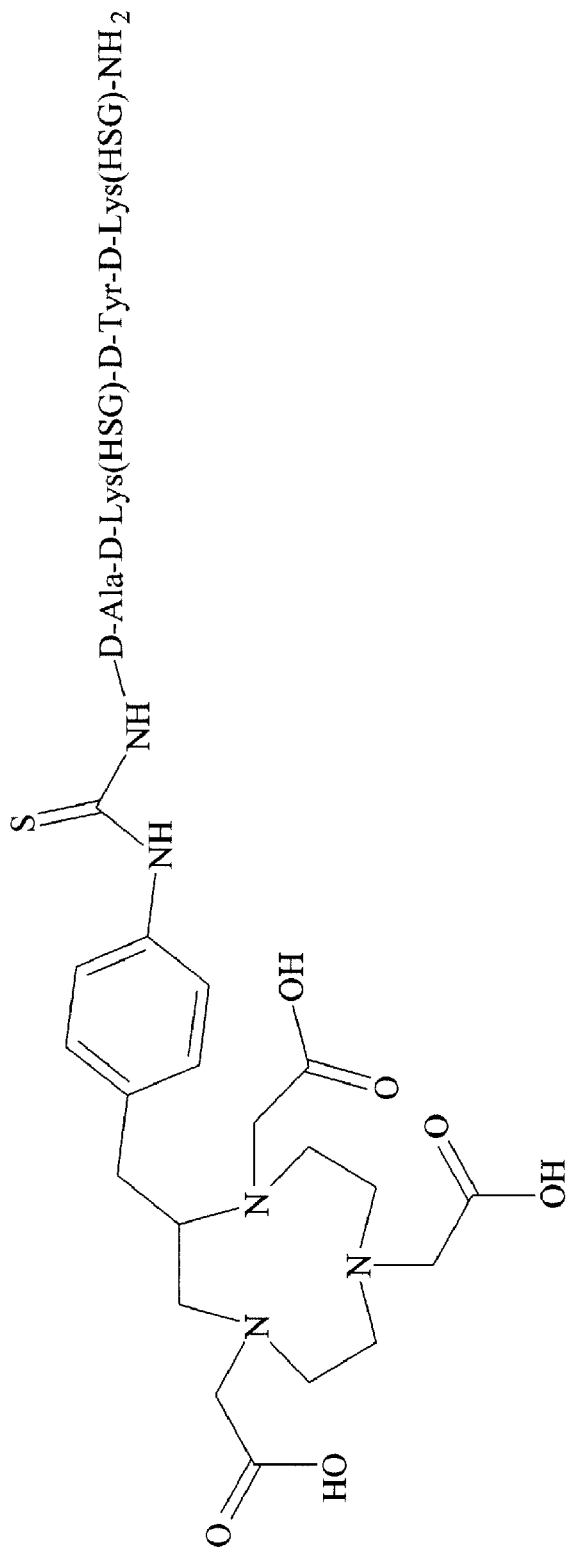
FIG. 15. Exemplary peptide IMP 449.
Figure 16:
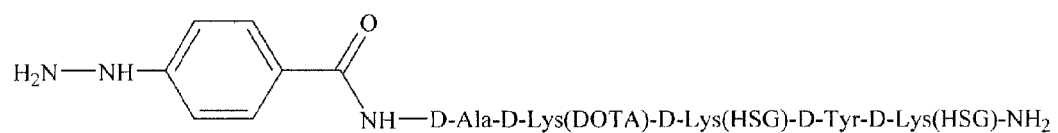
FIG. 16. Additional exemplary peptides IMP 422, IMP 426 and IMP 428.
Figure 16:
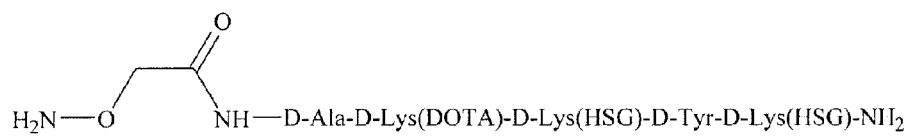
Figure 16:
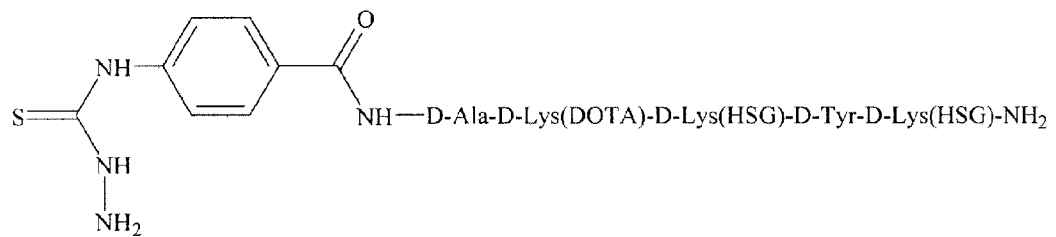

Further examples of peptides of possible use are shown in FIGS. 15 and 16. FIG. 16 shows the structures of IMP 422, IMP 426 and IMP 428. As discussed below, IMP 449 (FIG. 15) shows particular stability of the F-18 conjugated peptide under in vivo conditions, of use for labeling and imaging techniques.

Figure 17:
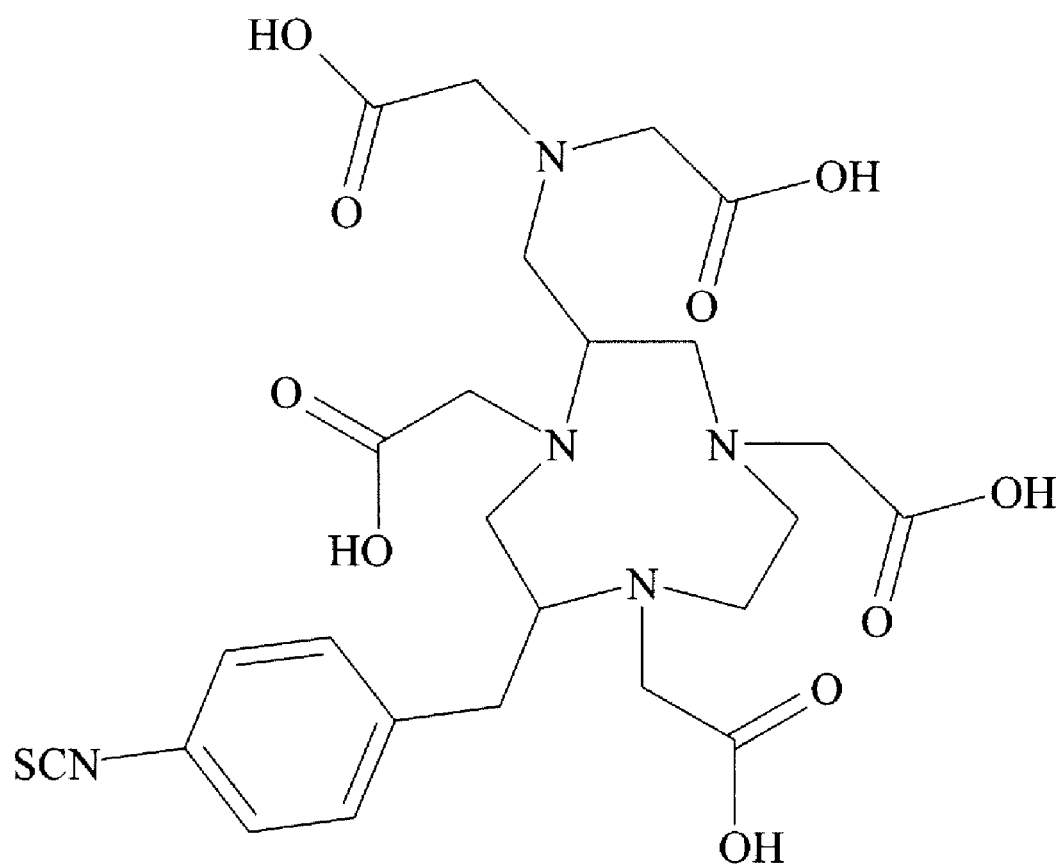
FIG. 17. Exemplary NOTA derivative.
Figure 18:
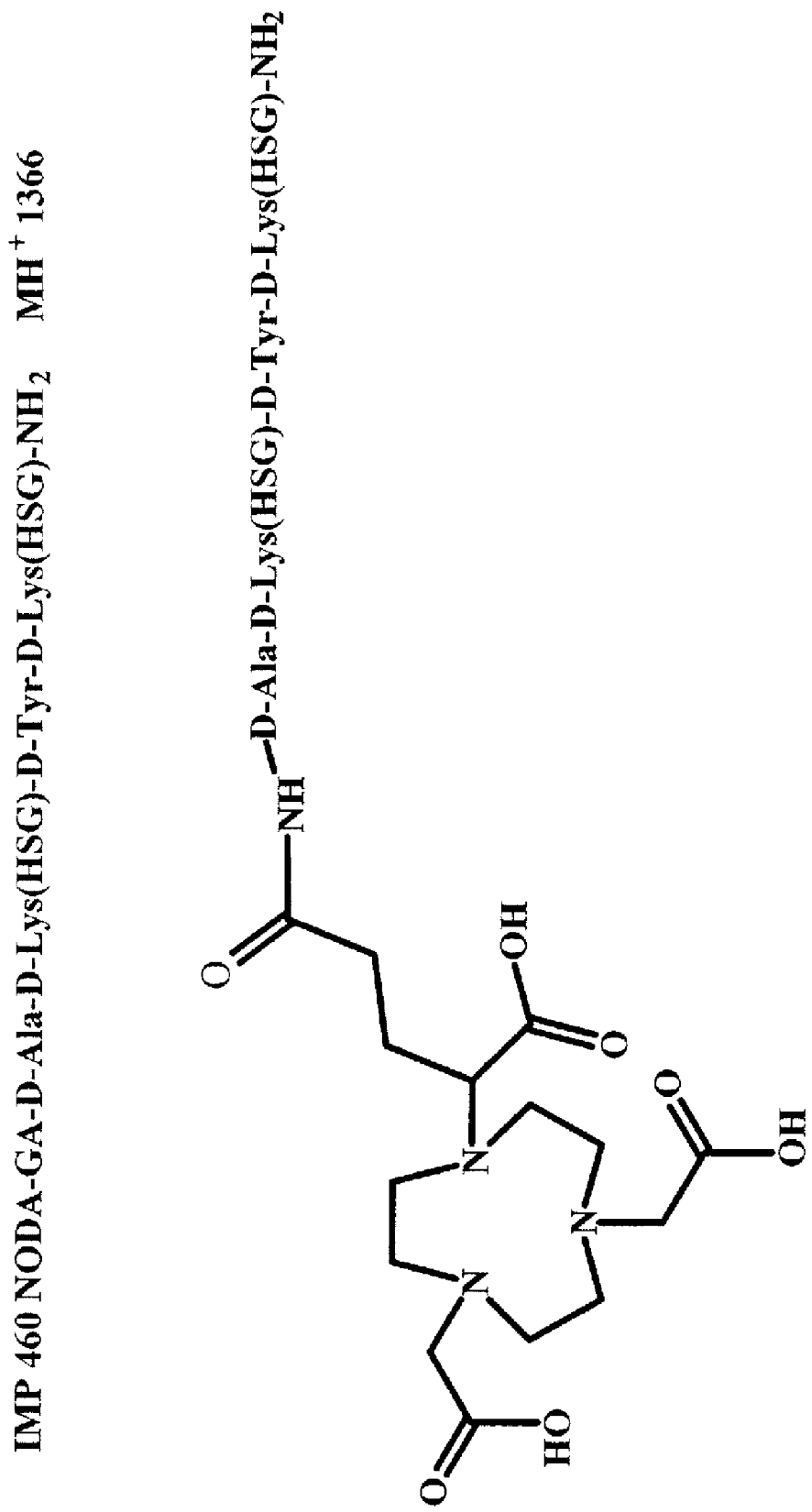
FIG. 18. Exemplary NODA-peptide structure.

FIG. 17 shows an alternative configuration for a NOTA type ligand. The NOTA moiety could be made from D or L para-nitrophenylalanine and the iminodiacetic acid portion would come from diaminopropionic acid, which could be D or L. Furthermore, the position of the ethylene bridge could be switched with the diaminopropionic acid to give a different configuration of groups on the ligand. All of these modifications could affect binding kinetics and stability of the complex, which is subsequently formed. FIG. 18 illustrates the structure of a NODA-Ga peptide that could be labeled with, for example, Ga-68 or F-18.

In certain embodiments, alternative chelating moieties may be used to bind to $^{18}$F-metal or $^{18}$F-boron complexes. FIG. 22A-D illustrates some exemplary potential chelating moieties based on the structure of NETA. As discussed above, Chong et al. (2007) report that NETA ligands may show improved serum stability when complexed with various metals. Chelator design may also be optimized to increase the binding affinity of the peptide for $^{18}$F-metal.

Results of Peptide Labeling Screening Study

Most of the DTPA derivatives showed labeling comparable to the labeling of IMP 272. There were exceptions, IMP 349, bearing the bisphosphonate group on a cysteine side chain, labeled very poorly. The DOTA ligand did not bind the Al-$^{18}$F. The ITC DTPA ligand of IMP 326 did not bind the Al-$^{18}$F as well as DTPA. The NTA ligand of IMP 331 did not bind the Al-$^{18}$F. The EDTA ligand of IMP 332 bound the Al-$^{18}$F but not as well as the DTPA. Symmetrical DTPA ligand did not bind the Al-$^{18}$F. The phosphonates and phosphate groups tested did not bind Al-$^{18}$F well under the conditions tested. The screen did show that a group that was attached near the DTPA could influence the stability of the Al-$^{18}$F-DTPA complex. The screen showed that IMP 375 labeled better and formed a complex that was significantly more stable than IMP 272. IMP 375 labeled well and was stable in water, showing 95.4% remaining bound after 5 hours at 25° C. (not shown). For in vivo use a peptide with high serum stability would be preferred.

The peptide labeling screening study only looked at the binding of Al-$^8$F. Some of the peptides that did not label well with Al-$^8$F might label better with another metal binding to the F-18.

Peptide Synthesis

The peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (US Patent Application Pub. No. US 2005/0002945 A1, application Ser. No. 10/776,470, Pub. Date. Jan. 6, 2005). The tri-t-butyl DOTA, symmetrical tetra-t-butyl DTPA and ITC-benzyl DTPA were obtained from MACROCYCLICS®. The Aloc/Fmoc Lysine and Dap (diaminopropionic acid derivatives (also Dpr)) were obtained from CREOSALUS® or BACHEM®. The Sieber Amide resin was obtained from NOVABIOCHEM®. The remaining Fmoc amino acids were obtained from CREOSALUS®, BACHEM®, PEPTECH® or NOVABIOCHEM®.

IMP 272 was synthesized as described (McBride et al., US Patent Application Publ. No. 20040241158 A1, application Ser. No. 10/768,707, Dec. 2, 2004). IMP 288 was made as described (McBride et al., *J. Nucl. Med.* 2006, 47:1678-1688).

IMP 326 The hydrazine peptide (IMP 319) was made on Sieber amide resin using Fmoc-D-Lys(Aloc)-OH, Fmoc-D-Glu(OBut)-OH, Fmoc-D-Lys(Aloc)-OH, Fmoc-D-Tyr(But)-OH and 4-(Boc-NH—NH—)C$_6$H$_4$—CO$_2$H in that order. The 4-(Boc-NH—NH—)C$_6$H$_4$—CO$_2$H was made by adding Boc dicarbonate to 4-hydrazinobenzoic acid in a dioxane sodium hydroxide solution.

After the addition of the Boc-hydrazide the side chain Aloc groups were removed and the Trityl-HSG-OH groups were added to the side chains of the lysines. The peptide was then cleaved from the resin with TFA and purified by HPLC to obtain the desired hydrazine bis-HSG peptide IMP 319 (MH$^+$ 1201). The hydrazide peptide (0.0914 g) was then mixed with 0.0650 g of ITC-Benzyl DTPA in 3 mL of 0.1 M sodium phosphate pH 8.2. The pH of the solution was adjusted with 1 M NaOH to keep the pH at pH 8.2. After the reaction between the peptide and the ITC-Benzyl DTPA was complete the peptide conjugate was purified by HPLC.

IMP 329 The deferoxamine isothiocyanate was prepared by mixing 1.0422 g of deferoxamine mesylate (1.59×10$^{-3}$ mol) with 0.2835 g (1.59×10$^{-3}$ mol) of thiocarbonyldiimidazole in 10 mL of 1:1 methanol/water. Triethylamine, 0.23 mL was added and the reaction was purified by reverse phase HPLC after 2.5 hr to obtain the deferoxamine isothiocyanate MNa$^+$ 625.

The hydrazine peptide, IMP 319, (0.0533 g, 4.4×10$^{-5}$ mol, MH$^+$ 1201) was mixed with 0.0291 g of deferoxamine isothiocyanate in a sodium phosphate buffer at pH 8.1 for two hours then purified by HPLC to afford the desired product MH+ 1804.

IMP 331 The following amino acids were attached to Sieber amide resin (0.58 mmol/g) in the order shown; Fmoc-D-Lys(Aloc)-OH, Fmoc-D-Tyr(But)-OH and Fmoc-D-Lys(Aloc)-OH. The Aloc groups were removed and Trt-HSG-OH was added to the side chains of the lysines. The Fmoc was removed, then Fmoc-D-Ala-OH and Fmoc-Asp-OBut were added in that order (0.5 g of resin). The Fmoc was removed and the nitrogen of the Asp was alkylated overnight with 3 mL t-butyl bromoacetate and 3.6 mL diisopropylethylamine in 3.4 mL of NMP. The peptide was cleaved from the resin with TFA and purified by reverse phase HPLC to obtain the desired peptide MH$^+$ 1240.

IMP 332 The peptide was made on 3 g of Sieber amide resin (0.58 mmol/g). The following amino acids were added to the resin in the order shown: Fmoc-D-Lys(Aloc)-OH, Fmoc-D-Tyr(But)-OH, Fmoc-D-Lys(Aloc)-OH, Fmoc-D-Ala-OH, and Fmoc-Dpr(Fmoc)-OH. The resin was split into portions for subsequent syntheses. One gram of the resin was removed and the Fmoc groups were removed from the diaminopropionic acid. The peptide was alkylated overnight with 3 mL t-butyl bromoacetate, 3.6 mL diisopropylethyl amine and 3.4 mL NMP. The side chain Aloc groups were then removed and the Trt-HSG-OH groups were added. The peptide was then cleaved from the resin and purified by HPLC to obtain the product MH$^+$ 1327.

IMP 333 The peptide was made with 1 g of the same resin that was used to make IMP 332. The DTPA tetra-t-butyl ester (U.S. Publ. No. 20050002945) was added to both of the amines of the Dpr group. The Aloc groups were then removed and the Trt-HSG-OH was added. The peptide was then cleaved and purified by HPLC to obtain the desired product MH$^+$ 1845.

IMP 334 The peptide was made on 1 g Rink amide resin (0.7 mmol/g) with the following amino acids added in the order shown: Fmoc-D-Lys(Aloc)-OH, Fmoc-D-Glu(But)-OH, Fmoc-D-Lys(Aloc)-OH, Boc-Ser(But)-OH, The Aloc groups were removed and the Trityl-HSG-OH was added. The peptide was cleaved from the resin with TFA. The crude peptide was collected by precipitation from ether and dried. Sodium periodate, 0.33 g, was dissolved in 15 mL water. The crude peptide was dissolved in 1 mL 0.5 M sodium phosphate pH 7.6, 3 mL water and 1 mL of the periodate solution. 3 mL more periodate in one milliliter increments was added over ~2 hr. The mixture was then purified by reverse phase HPLC and lyophilized to obtain the aldehyde IMP 289 HCO—CO-D-Lys(HSG)-D-Glu-D-Lys(HSG)-NH$_2$ MH$^+$ 959. Alendronate (0.0295 g, CALBIOCHEM®) was dissolved in 150 μL 0.1 M NaOAc pH 4. The peptide, IMP 289, (0.0500 g) was dissolved in 100 μL of 13% isopropanol in water. Sodium cyanoborohydride was added and the mixture was purified by HPLC to afford the desired product MH$^+$ 1192.

IMP 337 & IMP 338 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, Fmoc-D-Ser(PO(OBzl)OH)—OH, and Ac$_2$O. The Aloc groups were removed and the Trt-HSG-OH groups were added to the side chains of the lysines. The peptide was cleaved from the resin and purified by HPLC to afford the desired products: IMP 337 MH$^+$ 1291 and IMP 338 MH$^+$ 1126.

IMP 345 The peptide was made on Sieber amide Resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, and tetra-t-butyl DTPA. The Aloc groups were removed and the Trt-HSG-OH groups were added to the side chains of the lysines. The peptide was cleaved from the resin and purified by HPLC to afford the desired product: IMP 345 MH$^+$ 1459.

IMP 349 The peptide IMP 347 DTPA-D-Cys-D-Ala-D-Lys(HSG)-D-Tyr-D-Lys(HSG)—NH$_2$ was made on Sieber amide Resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved Fmoc-D-Ala-OH, Fmoc-D-Cys(Trt)-OH and tetra-t-butyl DTPA were added. The peptide was cleaved from the resin and purified by HPLC to afford the desired product: IMP 347 MH$^+$ 1395. The peptide, IMP 347, 0.0446 g (3.2×10$^{-5}$ mol) was mixed with 0.4605 g (2.4×10$^{-3}$ mol) of ethenylidenebis (phosphonic acid) (Degenhardt et al., *J. Org. Chem.* 1986, 51:3488-3490) in 3 mL of water and the solution was adjusted to pH 6.5 with 1 M NaOH added dropwise. The reaction was stirred overnight and the reaction solution was adjusted to pH 1.49 by the addition of excess ethenylidenebis(phosphonic acid). The mixture was stirred overnight at room temperature and then purified by HPLC to obtain the desired peptide IMP 349 MH$^+$ 1583.

IMP 361 The peptide was made on Sieber amide resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved, Fmoc-D-Ala-OH, Fmoc-Dap(Aloc)-OH and tetra-t-butyl DTPA were added. The Aloc on the side chain of the Dap was removed and bromo acetyl was added with bromo acetic anhydride. The crude product was purified by HPLC to obtain the desired peptide IMP 361 (MH$^+$ 1498).

IMP 366 The peptide was made by the same method as IMP 361 with phenylthioacetic acid added last. The crude product was purified by HPLC to afford the product IMP 366 MH$^+$ 1528.

IMP 368 The peptide was as described for IMP 349 except the cysteine residue was not added and symmetrical tetra-t-butylDTPA (MACROCYCLICS®) was used in place of the unsymmetrical DTPA to obtain the desired product after purification, IMP 368 MH$^+$ 1292.

IMP 369 The peptide was made as described for IMP 349 with Fmoc-R-3-amino-3-(2-bromophenyl)propionic acid added in place of the D-Cys and symmetrical tetra-t-butylDTPA added in place of the unsymmetrical version to the DTPA tetra-t-butyl ester. The crude peptide was purified to obtain the desired product, MH$^+$ 1517.

IMP 370 The peptide was made as described for IMP 369 except Fmoc-R-3-amino-3-(2-nitrophenyl) propionic acid was used instead of the bromo. The desired product was obtained after purification by HPLC MH$^+$ 1484.

IMP 371 The peptide was made as described for IMP 370 except the unsymmetrical tetra-t-butyl DTPA was used in place of the of the symmetrical version. The desired product was obtained after purification by HPLC MH$^+$ 1484.

IMP 372 The peptide was made as described for IMP 361 with Fmoc-Ser(But)-OH used to attach the Ser to the Dap side chain. The Fmoc was removed and the peptide was cleaved from the resin and purified to obtain the desired product MH$^+$ 1465.

IMP 373 The peptide was made as described for IMP 361 with symmetrical-tetra-t-butylester DTPA used to attach the Sym-DTPA to the Dap side chain. The peptide was cleaved from the resin and purified to obtain the desired product MH$^+$ 1753.

IMP 374 The peptide was made as described for IMP 361 with Fmoc-5-ethyl cysteine added to the Dap side chain followed by chloro acetyl (on the cysteine nitrogen) added via chloroacetic anhydride. The peptide was cleaved from the resin and purified to obtain the desired product MH$^+$ 1585.

IMP 375 The peptide was made as described for IMP 361 with Fmoc-R-3-amino-3-(2-bromophenyl)propionic acid added to the Dap side chain followed by cleavage of the Fmoc group. The peptide was cleaved from the resin and purified to obtain the desired product MH+1603.

IMP 376 The peptide was made as described for IMP 361 with Fmoc-D-Tyr(But)-OH added after the second alanine followed by Fmoc-Cys($SO_3$H) and tetra-t-butylDTPA. The peptide was cleaved from the resin and purified to obtain the desired product MH+ 1558.

IMP 379 The peptide was made as described for IMP 361 with Boc-2-Abz-OH added to the side chain of the Dap. The peptide was cleaved from the resin and purified to obtain the desired product MH+ 1497.

IMP 382 The peptide was made as described for IMP 361 with the Aloc removed from the side chain of the Dap. The peptide was cleaved from the resin and purified to obtain the desired product MH+ 1378.

IMP 383 The peptide was made as described for IMP 361 with Fmoc-Gla(OBut)$_2$-OH added to the side chain of the Dap. The peptide was cleaved from the resin and purified to obtain the desired product MH+—$CO_2$ 1507

IMP 384 The peptide was made as described for IMP 361 with Fmoc-Boc-S-3-amino-3-(2-hydroxyphenyl)propionic acid added to the side chain of the Dap. The peptide was cleaved from the resin and purified to obtain the desired product MH+ 1541.

IMP 385 The peptide was made as described for IMP 361 with Fmoc-Dpr(Fmoc)-OH added to the side chain of the Dap. The peptide was cleaved from the resin and purified to obtain the desired product MH+ 1464.

IMP 386 The peptide was made as described for IMP 361 with Boc-D-2-pyridylalanine-OH added to the side chain of the Dap. The peptide was cleaved from the resin and purified to obtain the desired product MH+ 1526.

IMP 387 The peptide was made as described for IMP 361 with Fmoc-D-9-anthrylalanine-OH added to the side chain of the Dap. The peptide was cleaved from the resin and purified to obtain the desired product MH+ 1625.

IMP 389 The peptide was made as described for IMP 361 with bis-Boc-piperazine-2-carboxylate added to the side chain of the Dap. The peptide was cleaved from the resin and purified to obtain the desired product MH+ 1664.

Example 5

Alternative Methods for Preparing and Separating F-18 Labeled Peptides

In certain embodiments, heating is used to get the Al-F-18 complex into the NOTA chelating group. Alternatively, ITC benzyl NOTA (Macrocyclics) could be labeled with Al-F-18 and then conjugated to other heat sensitive molecules, such as proteins, after labeling. If high specific activity is needed the ITC Benzyl NOTA complex can be purified away from the cold ligand.

Al was added to the peptide and its HPLC profile compared to the empty NOTA peptide and the Al-F-18 peptide. The Al peptide and the Al-F-18 peptides have virtually the same retention time by HPLC, with ~1 min longer RT for the unlabeled peptide. The peptide was purified on a PHENOMENEX™ ONYX® monolithic C-18 100×4.5 mm column using a 3 mL/min flow rate. Buffer A was 0.1% TFA in water and Buffer B was 90% $CH_3CN$ 10% water and 0.1% TFA. The linear gradient went from 100% buffer A to 75:25 AB over 15 min. Since the Al complex co-elutes with the Al-F-18 complex, the amount of Al and F-18 added will determine the specific activity.

IMP 449 was prepared according to Example 7 below and labeled as follows. The F-18 was received in a 2.0 mL Fisher Microcentrifuge vial (02-681-374) containing 15 mCi of F-18 in ~325 µL in water. 3 µL of 2 mM $AlCl_3$ in 0.1 M pH 4 NaOAc was added to the F-18 solution and then vortex mixed. After about 4 min, 10 µL of 0.05 M IMP 449 in pH4 0.5 M NaOAc was added. The sample was vortex mixed again and heated in a 102° C. heating block for 17 min. The reaction was then cooled briefly and then the vial contents were removed and purified by HPLC as described above.

Separately, elution conditions were determined on the WATERS® ALLIANCE™ analytical system and the labeled peptide was eluted between 7.5 and 8.5 min. The analytical HPLC showed that the labeled peptide contained the Al-F IMP 449 (UV 220 nm) and did not contain the uncomplexed peptide, resulting in an increased specific activity.

The peptide was diluted in water and then pushed through a WAIERS® OASIS PLUS HLB™ extraction column. The labeled peptide was eluted with 3 mL of 1:1 EtOH/$H_2O$. HPLC analysis of the eluents confirmed that the column efficiently trapped the labeled peptide, which allowed the acetonitrile and TFA to be washed away from the peptide. The HPLC also showed that 1:1 EtOH/$H_2O$ eluent contained the desired product free of loose F-18 in a solvent suitable for injection after dilution. The apparent yield after purification was 11%.

Example 6

In-Vivo Studies

Nude mice bearing GW-39 human colonic xenograft tumors (100-500 mg) are injected with the bispecific antibody hMN-14×m679 ($1.5 \times 10^{-10}$ mol). The antibody is allowed to clear for 24 hr before the F-18 labeled HSG-bearing peptide (8.8 µCi, $1.5 \times 10^{-11}$ mol) is injected. The animals are imaged at 3, 24 and 48 hr post injection. The xenograft tumors are clearly imaged by PET scanning detection of the F-18 labeled peptide bound to the bispecific hMN-14×m679 that is localized to the tumors by binding of hMN-14 to tumor antigen.

Example 7

Production and Use of a Serum-Stable F-18 Labeled Peptide

IMP 449 NOTA-ITC benzyl-D-Ala-D-Lys(HSG)-D-Tyr-D-Lys(HSG)-$NH_2$ MH+ 1459 (FIG. 15)

The peptide, IMP 448 D-Ala-D-Lys(HSG)-D-Tyr-D-Lys(HSG)-$NH_2$ MH+ 1009 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757 g ($7.5 \times 10^{-5}$ mol) was mixed with 0.0509 g ($9.09 \times 10^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449, the desired product (FIG. 15).

F-18 Labeling of IMP 449

The peptide IMP 449 (0.002 g, $1.37 \times 10^{-6}$ mol) was dissolved in 686 µL (2 mM peptide solution) 0.1 M NaOAc pH 4.02. Three microliters of a 2 mM solution of Al in a pH 4 acetate buffer was mixed with 15 µL, 1.3 mCi of F-18. The solution was then mixed with 20 µL of the 2 mM IMP 449 solution and heated at 105° C. for 15 min. Reverse Phase HPLC analysis showed 35% (RT ~10 min) of the activity was attached to the peptide and 65% of the activity was eluted at the void volume of the column (3.1 min, not shown) indicating that the majority of activity was not associated with the peptide. The crude labeled mixture (5 µL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose F-18 Labeling

Further studies with purified IMP 449 demonstrated that the F-18 labeled peptide was highly stable (91%, not shown) in human serum at 37° C. for at least one hour and was partially stable (76%, not shown) in human serum at 37° C. for at least four hours. These results demonstrate that the F-18 labeled peptides disclosed herein exhibit sufficient stability under approximated in vivo conditions to be used for F-18 imaging studies.

F-18 ~21 mCi in ~400 µL of water was mixed with 9 µL of 2 mM $AlCl_3$ in 0.1 M pH 4 NaOAc. The peptide, IMP 449, 60 µL (0.01 M, $6 \times 10^{-7}$ mol in 0.5 NaOH pH 4.13) was added and the solution was heated at 110° C. for 15 min. The crude labeled peptide was then purified by placing the reaction solution in the barrel of a 1 cc WATERS® HLB column and eluting with water to remove unbound F-18 followed by 1:1 EtOH/H20 to elute the F-18 labeled peptide. The crude reaction solution was pulled through the column into a waste vial and the column was washed with three one milliliter fractions of water (18.97 mCi). The HLB column was then placed on a new vial and eluted with two×200 µL 1:1 EtOH/$H_2O$ to collect the labeled peptide (1.83 mCi). The column retained 0.1 mCi of activity after all of the elutions were complete. An aliquot of the purified F-18 labeled peptide (20 µL) was mixed with 200 µL of pooled human serum and heated at 37° C. Aliquots were analyzed by reverse phase HPLC (as described above). The results showed the relative stability of F-18 labeled purified IMP 449 at 37° C. at time zero, one hour (91% labeled peptide), two hours (77% labeled peptide) and four hours (76% labeled peptide) of incubation in human serum (not shown). It was also observed that F-18 labeled IMP 449 was stable in TFA solution, which is occasionally used during reverse phase HPLC chromatography. There appears to be a general correlation between stability in TFA and stability in human serum observed for the exemplary F-18 labeled molecules described herein. These results demonstrate that F-18 labeled peptide, produced according to the methods disclosed herein, shows sufficient stability in human serum to be successfully used for in vivo labeling and imaging studies, for example using PET scanning to detect labeled cells or tissues.

Example 8

In Vivo Biodistribution of F-18 Labeled IMP 449 in SCID Mice

F-18 labeled IMP 449 was prepared as described above (Example 7). The material was purified on an OASIS® HLB column (WATERS®, Milford, Mass.). The unbound material was washed out with water and the labeled peptide that was bound to the column was eluted with 1:1 ethanol:water mixture. Both fractions were analyzed by reverse phase C18 HPLC. The purified peptide eluted as several peaks on the reverse HPLC column (not shown). The unbound fraction collected from the OASIS® column showed poor recovery, 7%, from the C18 column (not shown).

The "unbound" fraction and the purified $^{18}$F-IMP 449 were injected into SCID mice that were previously injected with sc SU-DHL6 lymphoma cells. Only a few of the mice had visible tumors. Biodistribution data showed a significant difference between the "unbound" F-18 fraction and the purified $^{18}$F-IMP 449. Data are shown in Tables 4-6 below. Note that in this study, no pretargeting bispecific antibodies were administered to the animals before the labeled peptide. These results demonstrate the distribution of labeled peptide vs. free F-18 in vivo.

Unconjugated F-18 shows a high level of distribution to bone tissue in vivo. Uptake 20 minutes after injection was, as expected, seen primarily in the bone (spine), with about 12-15% injected dose per gram (ID/g), followed by the kidneys with about 4% ID/g. Localization of the F-18 label to bone tissue was substantially decreased by conjugation to a targeting peptide. When bound to IMP 449, uptake in the bone is reduced to ~1% ID/g at 20 min and 0.3% at 1 h after injection, with renal uptake of 11% at 20 min and 3.3% ID/g at 1 hr. Renal uptake of the peptide alone was similar to that of the pretargeted $^{18}$F-IMP 449 peptide (see following Example), suggesting its uptake was a function of the peptide rather than a consequence of the animals having been give the bsMAb 18 h earlier. Relatively low non-specific uptake was observed in the spine and femur with the F-18 labeled peptide compared with unbound F-18.

TABLE 4

F-18 "unbound" fraction at 20 min post injection:
% ID/g mean and the individual animals.

| Tissue | n | Mean | SD | Animal 1 | Animal 2 | Animal 3 |
|---|---|---|---|---|---|---|
| Tumor | 1 | — | — | 0.902 | — | — |
| Liver | 3 | 2.056 | 0.244 | 1.895 | 2.338 | 1.937 |
| Spleen | 3 | 1.869 | 0.434 | 1.677 | 2.366 | 1.564 |
| Kidney | 3 | 4.326 | 0.536 | 3.931 | 4.936 | 4.111 |
| Lung | 3 | 2.021 | 0.149 | 1.903 | 2.188 | 1.972 |
| Blood | 3 | 2.421 | 0.248 | 2.355 | 2.696 | 2.212 |
| Stomach | 3 | 0.777 | 0.409 | 0.421 | 1.224 | 0.687 |
| Small Int. | 3 | 2.185 | 0.142 | 2.042 | 2.325 | 2.187 |
| Large Int. | 3 | 1.403 | 0.069 | 1.482 | 1.356 | 1.372 |
| Femur | 3 | 11.688 | 1.519 | 11.502 | 13.292 | 10.270 |
| Spine | 3 | 14.343 | 2.757 | 17.506 | 13.072 | 12.452 |
| Muscle | 3 | 1.375 | 0.160 | 1.191 | 1.457 | 1.478 |

TABLE 5

$^{18}$F-IMP 449 purified, 80 µCi, $1 \times 10^{-8}$ mol at 20 min post injection:
% ID/g mean and the individual animals

| Tissue | n | Mean | SD | Animal 1 | Animal 2 | Animal 3 | Animal 4 | Animal 5 |
|---|---|---|---|---|---|---|---|---|
| Tumor | 1 | — | — | 0.891 | — | — | — | — |
| Liver | 5 | 2.050 | 0.312 | 1.672 | 1.801 | 2.211 | 2.129 | 2.440 |
| Spleen | 5 | 1.297 | 0.259 | 0.948 | 1.348 | 1.144 | 1.621 | 1.425 |

TABLE 5-continued $^{18}$F-IMP 449 purified, 80 µCi, 1 × 10$^{-8}$ mol at 20 min post injection:
% ID/g mean and the individual animals

| Tissue | n | Mean | SD | Animal 1 | Animal 2 | Animal 3 | Animal 4 | Animal 5 |
|---|---|---|---|---|---|---|---|---|
| Kidney | 5 | 12.120 | 4.128 | 8.354 | 7.518 | 12.492 | 15.535 | 16.702 |
| Lung | 5 | 2.580 | 0.518 | 2.034 | 2.103 | 2.804 | 2.678 | 3.278 |
| Blood | 5 | 3.230 | 0.638 | 2.608 | 2.524 | 3.516 | 3.512 | 3.992 |
| Stomach | 5 | 1.017 | 0.907 | 0.805 | 0.775 | 0.344 | 0.557 | 2.605 |
| Small Int. | 5 | 1.212 | 0.636 | 0.896 | 0.921 | 0.927 | 0.967 | 2.349 |
| Large Int. | 5 | 0.709 | 0.220 | 0.526 | 0.568 | 0.599 | 0.793 | 1.057 |
| Femur | 5 | 0.804 | 0.389 | 0.314 | 0.560 | 1.280 | 0.776 | 1.087 |
| Spine | 5 | 3.915 | 6.384 | 0.819 | 0.923 | 1.325 | 1.177 | 15.330# |
| Muscle | 5 | 0.668 | 0.226 | 0.457 | 0.439 | 0.960 | 0.673 | 0.814 |

High spine uptake in Animal #5 was confirmed by recounting.

TABLE 6

$^{18}$F-IMP 449 purified, 80 µCi, 1 × 10$^{-8}$ mol at 1 h post injection:
% ID/g mean and the individual animals

| Tissue | n | Mean | SD | Animal 1 | Animal 2 | Animal 3 | Animal 4 |
|---|---|---|---|---|---|---|---|
| Tumor | 1 | 0.032 | 0.064 | 0.000 | 0.127 | 0.000 | 0.000 |
| Liver | 4 | 0.883 | 0.308 | 1.103 | 0.632 | 0.604 | 1.191 |
| Spleen | 4 | 1.061 | 0.702 | 1.598 | 0.631 | 0.301 | 1.713 |
| Kidney | 4 | 3.256 | 0.591 | 3.606 | 2.392 | 3.362 | 3.666 |
| Lung | 4 | 0.324 | 0.094 | 0.411 | 0.232 | 0.256 | 0.399 |
| Blood | 4 | 0.285 | 0.104 | 0.378 | 0.153 | 0.250 | 0.358 |
| Stomach | 4 | 0.152 | 0.082 | 0.225 | 0.041 | 0.199 | 0.142 |
| Small Int. | 4 | 1.290 | 0.228 | 1.124 | 1.247 | 1.166 | 1.624 |
| Large Int. | 4 | 0.115 | 0.035 | 0.167 | 0.091 | 0.094 | 0.109 |
| Femur | 4 | 1.006 | 0.876 | 2.266 | 0.448 | 0.939 | 0.374 |
| Spine | 4 | 0.314 | 0.076 | 0.423 | 0.257 | 0.268 | 0.306 |
| Muscle | 4 | 0.591 | 0.946 | 0.205 | 0.077 | 2.008 | 0.075 |

We conclude that the F-18 labeled peptide showed sufficient in vivo stability to successfully perform labeling and imaging studies.

Example 9

In Vivo Studies with Pretargeting Antibody

F-18 labeled IMP 449 was prepared as follows. The F-18, 54.7 mCi in ~0.5 mL was mixed with 3 µL 2 mM Al in 0.1 M NaOAc pH 4 buffer. After 3 min, 10 µL of 0.05 M IMP 449 in 0.5 M pH 4 NaOAc buffer was added and the reaction was heated in a 96° C. heating block for 15 min. The contents of the reaction were removed with a syringe. The crude labeled peptide was then purified by HPLC on a Phenomenex Onyx monolithic C18, 100×4.6 mm column part. No. CH0-7643. The flow rate was 3 mL/min. Buffer A was 0.1% TFA in water and Buffer B was 90% acetonitrile in water with 0.1% TFA. The gradient went from 100% A to 75/25 A:B over 15 min. There was about 1 min difference in RT between the labeled peptide, which eluted first and the unlabeled peptide. The HPLC eluent was collected in 0.5 min fractions. The labeled peptide came out between 6 to 9 min depending on the HPLC used. The HPLC purified peptide sample was further processed by diluting the fractions of interest two fold in water and placing the solution in the barrel of a 1 cc Waters HLB column. The cartridge was eluted with 3×1 mL water to remove acetonitrile and TFA followed by 400 µL 1:1 EtOH/H20 to elute the F-18 labeled peptide.

The purified $^{18}$F-IMP 449 eluted as a single peak on an analytical HPLC C18 column.

Taconic nude mice bearing the four slow-growing sc CaPan1 xenografts were used. Three of the mice were injected with TF10 (162 µg) followed with $^{18}$F-IMP 449 18 h later. TF10 is a humanized bispecific antibody of use for tumor imaging studies, with divalent binding to the PAM-4 defined MUC 1 tumor antigen and monovalent binding to HSG (see, e.g., Gold et al., 2007, J. Clin. Oncol. 25(18S): 4564). One mouse was injected with peptide alone. All of the mice were necropsied 1 h post peptide injection. Tissues were counted immediately. Animal #2 showed high counts in the femur. The femur was transferred into a new vial and was recounted along with the old empty vial. Recounting indicated that the counts were on the tissue. This femur was broken and had a large piece of muscle attached to it. Comparison of mean distributions showed substantially higher levels of F-18-labeled peptide localized in the tumor than in any normal tissues in the presence of tumor-targeting bispecific antibody.

Tissue uptake was similar in animals given the $^{18}$F-IMP 449 alone or in a pretargeting setting. Uptake in the human pancreatic cancer xenograft, CaPan1, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

TABLE 7

Tissue uptake at 1 h post peptide injection,
mean and the individual animals:

| | TF10 (162 µg) -→18 h → $^{18}$F IMP449 (10:1) | | | | | $^{18}$F IMP 449 alone |
|---|---|---|---|---|---|---|
| Tissue | n | Mean | SD | Animal 1 | Animal 2 | Animal 3 | Animal 1 |
| Tumor (mass) | 3 | 4.591 | 0.854 | 4.330 (0.675 g) | 5.546 (0.306 g) | 3.898 (0.353 g) | 0.893 (0.721 g) |
| Liver | 3 | 0.197 | 0.041 | 0.163 | 0.242 | 0.186 | 0.253 |
| Spleen | 3 | 0.202 | 0.022 | 0.180 | 0.224 | 0.200 | 0.226 |
| Kidney | 3 | 5.624 | 0.531 | 5.513 | 6.202 | 5.158 | 5.744 |
| Lung | 3 | 0.421 | 0.197 | 0.352 | 0.643 | 0.268 | 0.474 |
| Blood | 3 | 0.196 | 0.028 | 0.204 | 0.219 | 0.165 | 0.360 |
| Stomach | 3 | 0.123 | 0.046 | 0.080 | 0.172 | 0.118 | 0.329 |
| Small Int. | 3 | 0.248 | 0.042 | 0.218 | 0.295 | 0.230 | 0.392 |
| Large Int. | 3 | 0.141 | 0.094 | 0.065 | 0.247 | 0.112 | 0.113 |
| Pancreas | 3 | 0.185 | 0.078 | 0.259 | 0.194 | 0.103 | 0.174 |
| Spine | 3 | 0.394 | 0.427 | 0.140 | 0.888 | 0.155 | 0.239 |
| Femur | 3 | 3.899 | 4.098 | 2.577 | 8.494* | 0.625 | 0.237 |
| Brain | 3 | 0.064 | 0.041 | 0.020 | 0.072 | 0.100 | 0.075 |
| Muscle | 3 | 0.696 | 0.761 | 0.077 | 1.545 | 0.465 | 0.162 |

*High counts in Animal # 2 femur were confirmed by recounting after transferring femur into a new vial. Animal #2 showed higher uptake in normal tissues than Animals #1 and #3.

Example 10

Comparison of Biodistribution of $^{111}$In-IMP 449 vs. $^{18}$F-IMP 449 with Pretargeting Antibody The goal of the study was to compare biodistribution of $^{111}$In-IMP 449 and $^{18}$F-IMP 449 in nude mice bearing sc LS174 T xenografts after pretargeting with bispecific antibody TF2. TF2 antibody was made by the dock-and-lock method and contains binding sites for the CEA tumor antigen and the HSG hapten (see, e.g., Sharkey et al., Radiology 2008, 246:497-507; Rossi et al., PNAS USA 2006, 103:6841-46). Since there were insufficient numbers of mice with tumors at one time, the study was performed on 2 different weeks.

$^{111}$In-IMP 449: $^{111}$In labeling was performed using a procedure similar to the one used for labeling IMP 288, except at lower specific activity. ITLC and C-18 RP HPLC showed ~30% unbound (not shown). The labeled peptide was purified on an HLB column (1 mL, 30 mg). The analyses of the purified product again showed 33% unbound (top 20% of strip) by ITLC developed in saturated sodium chloride. RP HPLC showed multiple peaks before and after purification (not shown). SE HPLC after purification showed 47% of the activity shift to HMW when mixed with 20× molar excess of TF2 (not shown).

$^{18}$F-IMP 449: Labeling was performed as described above except the F-18 was purified on a QMA cartridge before labeling as described by others (Kim et. al. Applied Radiation and Isotopes 61, 2004, 1241-46). Briefly, the Sep-Pak® Light Waters Accell™ Plus QMA Cartridge was prepared flushed with 10 mL 0.4 M KHCO$_3$ and then washed with 10 mL DI water. The $^{18}$F (42 mCi) in 2 mL water was loaded onto the QMA cartridge. The cartridge was eluted with 10 mL DI water to remove impurities. The column was then eluted with 1 mL 0.4 M KHCO$_3$ in 200 μL fractions. Fraction number two contained the bulk of the activity, 33 mCi. The pH of the F-18 solution was then adjusted with 10 μL of glacial acetic acid. The $^{18}$F from fraction #2 was then mixed with 3 μL of 2 mM Al in 0.1 M pH 4 NaOAc buffer. The sample was then mixed with 10 μL of 0.05 M IMP 449 in 0.5 M NaOAc buffer at pH4 and the reaction solution was heated at 94° C. for 15 min. The $^{18}$F-IMP 449 was purified by RP HPLC. The fraction containing the product was put through an HLB column to exchange the buffer. The column was washed with water after loading the sample. The product was eluted with 1:1 water: ethanol in a 400 volume. RP HPLC of the product showed one major peak with a shoulder (not shown). Since the yield was low, the specific activity was low and more peptide was injected into mice, resulting in a bsMAb:peptide ratio of 6.9:1 instead of 10:1.

Results

The labeling of IMP 449 with In-111 resulted in multiple products. Possibly some might be binuclear complexes. The $^{111}$In-IMP 449 showed high kidney uptake and high blood concentration. However, even as multiple species, $^{111}$In-IMP 449 showed localization to the tumor when pretargeted with TF2 (FIG. 19).

Figure 19:
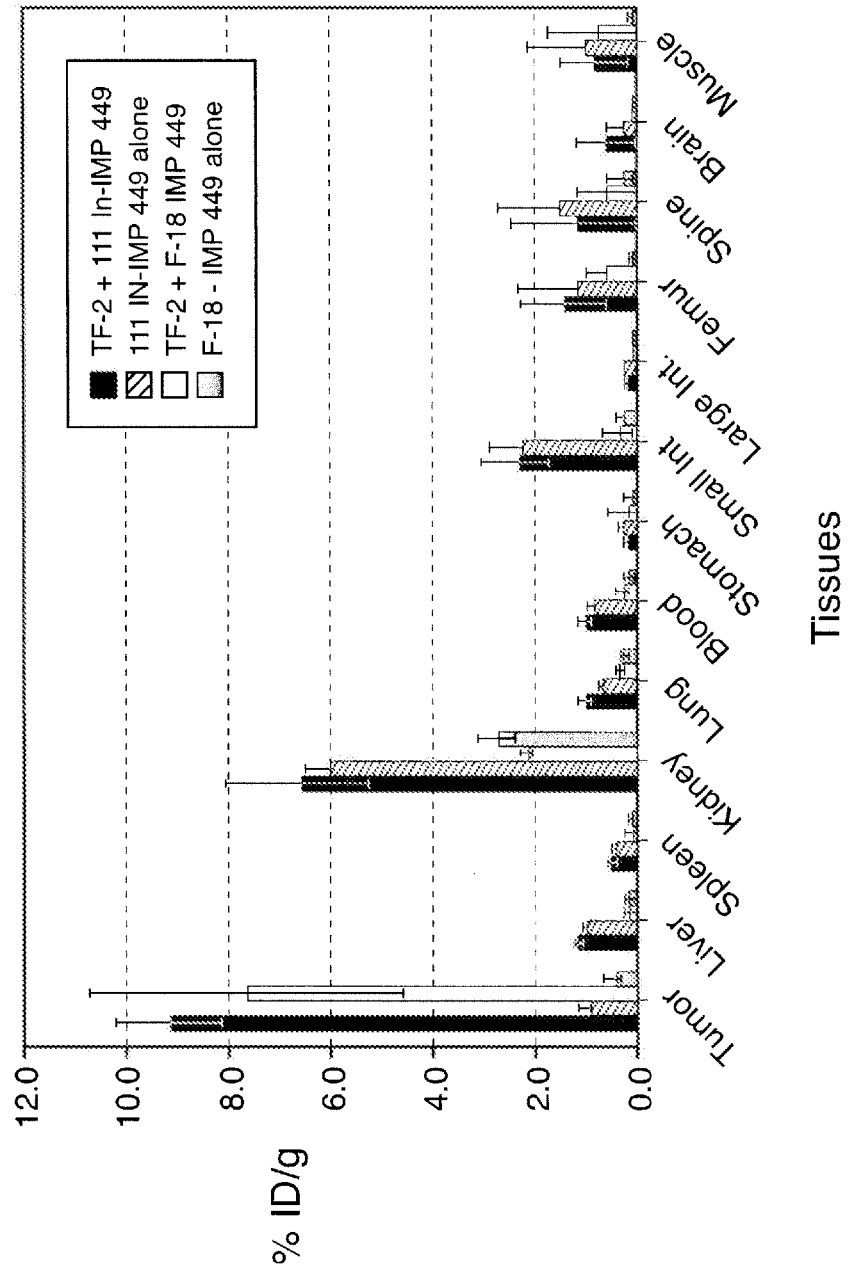
FIG. 19. Comparative biodistribution of In-111 and F-18 labeled IMP 449 in mice with or without TF2 bispecific antibody.

FIG. 19 shows the comparative biodistribution of In-111 and F-18 labeled IMP 449 in mice. Both labeled peptides showed similarly high levels of localization to tumor tissues in the presence of the bispecific TF2 antibody. The In-111 labeled species showed higher concentration in kidney than the F-18 labeled species in the presence or absence of TF2 antibody. The data are summarized in Tables 8-11 below.

TABLE 8

Mice were injected with TF2 (163.2ug, 1.035 × 10$^{-9}$ mol) iv followed with $^{111}$In IMP 449 (1.035 × 10$^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 9.18 | 1.02 | 9.22 | 8.47 | 8.04 | 9.45 | 10.70 |
| Liver | 5 | 1.15 | 0.09 | 1.03 | 1.25 | 1.20 | 1.21 | 1.08 |
| Spleen | 5 | 0.48 | 0.06 | 0.43 | 0.49 | 0.58 | 0.50 | 0.42 |
| Kidney | 5 | 6.63 | 1.38 | 8.81 | 6.21 | 7.03 | 5.85 | 5.23 |
| Lung | 5 | 1.03 | 0.14 | 0.92 | 1.14 | 1.18 | 1.04 | 0.86 |
| Blood | 5 | 0.99 | 0.15 | 1.04 | 1.13 | 1.12 | 0.83 | 0.83 |
| Stomach | 5 | 0.16 | 0.05 | 0.25 | 0.17 | 0.16 | 0.13 | 0.12 |
| Small Int. | 5 | 2.33 | 0.65 | 2.21 | 2.51 | 2.01 | 3.33 | 1.59 |
| Large Int. | 5 | 0.20 | 0.04 | 0.21 | 0.25 | 0.18 | 0.21 | 0.14 |
| Femur | 5 | 1.45 | 0.87 | 0.59 | 1.30 | 0.71 | 2.02 | 2.62 |
| Spine | 5 | 1.18 | 1.23 | 0.89 | 3.35 | 0.76 | 0.47 | 0.43 |
| Brain | 5 | 0.14 | 0.16 | 0.05 | 0.06 | 0.13 | 0.04 | 0.43 |
| Muscle | 5 | 0.83 | 0.66 | 0.25 | 1.30 | 0.23 | 0.65 | 1.73 |
| Body Wt. | 5 | 25.49 | 1.41 | 27.89 | 24.14 | 25.27 | 25.10 | 25.06 |

TABLE 9

A group of 2 mice were injected with $^{111}$In IMP 449 (1.035 × 10$^{-10}$ mol) without pretargeting antibody. Peptide tissue uptake (% ID/g) at 1 h post peptide injection is shown below.

| Tissue | n | Mean | SD | Animal 1 | Animal 2 |
|---|---|---|---|---|---|
| Tumor | 2 | 0.922 | 0.195 | 0.784 | 1.060 |
| Liver | 2 | 1.033 | 0.048 | 0.999 | 1.067 |
| Spleen | 2 | 0.409 | 0.067 | 0.362 | 0.456 |
| Kidney | 2 | 6.046 | 0.449 | 5.729 | 6.364 |
| Lung | 2 | 0.695 | 0.032 | 0.672 | 0.717 |
| Blood | 2 | 0.805 | 0.182 | 0.934 | 0.676 |
| Stomach | 2 | 0.290 | 0.055 | 0.251 | 0.329 |
| Small Int. | 2 | 2.234 | 0.594 | 1.814 | 2.654 |
| Large Int. | 2 | 0.237 | 0.022 | 0.253 | 0.222 |
| Femur | 2 | 1.210 | 1.072 | 1.968 | 0.453 |
| Spine | 2 | 1.463 | 1.213 | 2.320 | 0.605 |
| Brain | 2 | 0.133 | 0.091 | 0.068 | 0.197 |
| Muscle | 2 | 1.005 | 1.148 | 1.817 | 0.193 |
| Body Wt. | 2 | 26.65 | 3.19 | 28.90 | 24.39 |

TABLE 10

Mice were injected with TF2 (163.2ug, 1.035 × 10$^{-9}$ mol) iv followed with $^{18}$F-IMP 449 (1.5 × 10$^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 7.624 | 3.080 | 5.298 | 7.848 | 12.719 | 5.118 | 7.136 |
| Liver | 5 | 0.172 | 0.033 | 0.208 | 0.143 | 0.196 | 0.131 | 0.180 |
| Spleen | 5 | 0.142 | 0.059 | 0.239 | 0.081 | 0.132 | 0.118 | 0.140 |
| Kidney | 5 | 2.191 | 0.125 | 2.313 | 2.141 | 2.154 | 2.319 | 2.027 |
| Lung | 5 | 0.315 | 0.094 | 0.474 | 0.230 | 0.300 | 0.305 | 0.265 |
| Blood | 5 | 0.269 | 0.143 | 0.431 | 0.395 | 0.132 | 0.126 | 0.260 |
| Stomach | 5 | 0.218 | 0.341 | 0.827 | 0.041 | 0.098 | 0.054 | 0.070 |
| Small Int. | 5 | 0.351 | 0.313 | 0.903 | 0.185 | 0.297 | 0.170 | 0.198 |
| Large Int. | 5 | 0.069 | 0.028 | 0.076 | 0.043 | 0.111 | 0.073 | 0.042 |
| Femur | 5 | 0.625 | 0.358 | 0.869 | 0.146 | 0.811 | 0.957 | 0.344 |
| Spine | 5 | 0.585 | 0.569 | 0.159 | 0.119 | 0.493 | 1.526 | 0.626 |
| Brain | 5 | 0.029 | 0.005 | 0.033 | 0.021 | 0.035 | 0.026 | 0.028 |
| Muscle | 5 | 0.736 | 0.970 | 0.190 | 0.064 | 0.494 | 2.438 | 0.496 |
| Body Wt. | 5 | 24.69 | 1.20 | 23.05 | 26.36 | 24.45 | 24.48 | 25.11 |

TABLE 11

Mice were injected with $^{18}$F-IMP 449 (1.5 × 10$^{-10}$ mol) without pretargeting antibody. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 0.472 | 0.201 | 0.256 | 0.344 | 0.533 | 0.447 | 0.779 |
| Liver | 5 | 0.177 | 0.035 | 0.141 | 0.200 | 0.141 | 0.185 | 0.217 |
| Spleen | 5 | 0.118 | 0.027 | 0.098 | 0.094 | 0.101 | 0.144 | 0.151 |
| Kidney | 5 | 2.727 | 0.367 | 2.430 | 2.452 | 2.500 | 3.080 | 3.173 |
| Lung | 5 | 0.246 | 0.082 | 0.206 | 0.209 | 0.156 | 0.301 | 0.358 |
| Blood | 5 | 0.167 | 0.072 | 0.110 | 0.135 | 0.104 | 0.217 | 0.267 |
| Stomach | 5 | 0.114 | 0.083 | 0.149 | 0.241 | 0.037 | 0.067 | 0.074 |
| Small Int. | 5 | 0.277 | 0.081 | 0.407 | 0.286 | 0.206 | 0.213 | 0.271 |
| Large Int. | 5 | 0.072 | 0.029 | 0.061 | 0.052 | 0.047 | 0.083 | 0.118 |
| Femur | 5 | 0.100 | 0.032 | 0.080 | 0.144 | 0.110 | 0.109 | 0.059 |
| Spine | 5 | 0.305 | 0.268 | 0.104 | 0.647 | 0.099 | 0.132 | 0.545 |
| Brain | 5 | 0.034 | 0.025 | 0.018 | 0.018 | 0.022 | 0.034 | 0.077 |
| Muscle | 5 | 0.088 | 0.022 | 0.087 | 0.069 | 0.069 | 0.122 | 0.092 |
| Body Wt. | 5 | 25.34 | 1.72 | 25.05 | 26.88 | 26.40 | 25.88 | 22.51 |

In summary, a simple, reproducible method and compositions are described herein for producing F-18 labeled targeting peptides that are suitable for use in in vivo imaging of a variety of disease states. The skilled artisan will realize that the bispecific antibodies disclosed above are not limiting, but may comprise any known antibodies against a wide variety of disease or pathogen target antigens. Nor is the method limited to pretargeting with bispecific antibodies. In other embodiments, molecules or complexes that directly bind to target cells, tissues or organisms to be imaged may be labeled with F-18 using the methods disclosed herein and administered to a subject for PET imaging (see Examples below).

The Al-F-18 labeled peptides, exemplified by IMP 449, are sufficiently stable under in vivo conditions to be utilized in known imaging protocols, such as PET scanning. The present yield of radiolabeled peptide prepared as described above varies between 5 and 20%, and even with a brief HPLC purification step to separate labeled from unlabeled peptide the final yield is about 5%. Further, the claimed methods result in preparation of F-18 labeled targeting peptides that are ready for injection within 1 hour of preparation time, well within the decay time of F-18 to allow suitable imaging procedures to be performed. Finally, the described and claimed methods result in minimal exposure of the operator to radioisotope exposure, compared with known methods of preparing F-18 labeled compounds for imaging studies.

Example 11

F-18 Labeling Kit

An F-18 labeling kit was made by mixing 8.0 mg of IMP 449 with 0.1549 g of ascorbic acid. The two reagents were dissolved in 10.5 mL water and the solution was dispensed in 1.0 mL aliquots into 10 vials. The pH was not adjusted. The solutions were frozen, lyophilized and sealed under vacuum.

Example 12

Imaging of Tumors In Vivo Using Labeled Peptides and Pretargeting with Bispecific Antibodies The present Examples show that in vivo imaging techniques using pretargeting with bispecific antibodies and labeled targeting peptides may be used to successfully detect tumors of relatively small size. The pretargeting antibodies utilized were either TF2, described above, or the TF10 antibody.

Formulation Buffer:

The formulation buffer was made by mixing 0.3023 g ascorbic acid, 18.4 mL DI water and 1.6 mL 1 M NaOH to adjust the pH to 6.61. The buffer was dispensed in 1 mL aliquots into 20 vials and lyophilized.

The F-18 was purified on a WATERS® ACCELL™ Plus QMA Light cartridge according to the literature procedure, wherein the cartridge was washed with 10 mL 0.4 M $KHCO_3$ followed by a 10 mL wash with DI water. The F-18 in 2 mL of water was pushed through the cartridge and then washed with 10 mL of water. The F-18 was then eluted from the cartridge in 5×200 μL aliquots with 0.4 M $KHCO_3$. Most of the activity was eluted in the second fraction. The activity in the second fraction was mixed with 3 μL 2 mM Al in a pH 4 acetate buffer. The Al-F-18 solution was then injected into the ascorbic acid IMP 449 labeling vial and heated to 105° C. for 15 min. The reaction solution was cooled and mixed with 0.8 mL DI water. The reaction contents were placed on a WATERS® OASIS® 1 cc HLB Column and eluted into a waste vial. The column was washed with 3×1 mL DI water. The column was transferred to a formulation vial containing ascorbic acid. The column was eluted with 2×200 μL 1:1 $EtOH/H_2O$ to elute the labeled peptide.

Production of TF10 Bispecific Antibody Using DNL Technology

The cancer-targeting antibody component in TF10 is derived from hPAM4, a humanized anti-MUC1 MAb that has been studied as a radiolabeled MAb in detail (e.g., Gold et al., *Clin. Cancer Res.* 13: 7380-7387, 2007). The hapten-binding component is derived from h679, a humanized anti-histaminyl-succinyl-glycine (HSG) MAb discussed above. The TF10 bispecific ([hPAM4]$_2$×h679) antibody was produced using the method disclosed for production of the (anti CEA)$_2$×anti HSG bsAb TF2 (Rossi et al., 2006). The TF10 construct bears two humanized PAM4 Fabs and one humanized 679 Fab.

For TF10, a Fab of the humanized hPAM4 antibody was linked using a peptide spacer to an α-sequence. The α-sequence is unique because it spontaneously associates with another α-sequence to form a dimer. In TF10, the structure contains 2 hPAM4 anti-MUC1 Fabs linked together by the 2α-sequences (called hPAM4-DDD). The other component of TF10 is produced by linking a β-sequence to the Fab' of the humanized anti-HSG antibody. Unlike the α-sequence, the β-sequence does not self-associate, but instead binds to the dimeric structure formed by the 2α-sequences (h679-AD). Thus, when these 2 separately produced proteins are mixed together, they immediately form an 'a$_2$b' structure, with each Fab' oriented in a manner to allow unimpeded binding to its antigen. The stability of this binding interaction has been further improved by strategically positioning cysteine in each of the α- and β-sequences (2 in the β-sequence and 1 in the α-sequence). Because 'b' binds to 'a$_2$' in a highly specific orientation, once a$_2$b is assembled, disulfide bridges can form between the α- and β-moieties, thereby covalently attaching these 2 proteins. Both the α- and β-sequences are found in human proteins, and therefore are not expected to add to the immunogenicity of the complex.

The anti-MUC1 fusion protein hPAM4-α was generated by fusion of the α sequence to the C-terminal end of the Fd chain. The anti-HSG fusion protein h679-β was formed by linking the β sequence to the C-terminal end of the Fd chain. The stably tethered, multivalent bsMAb TF10 was formed by pairing the hPAM4-α with the h679-β.

The two fusion proteins (hPAM4-DDD and h679-AD2) were expressed independently in stably transfected myeloma cells. The tissue culture supernatant fluids were combined, resulting in a two-fold molar excess of hPAM4-α. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

A full tissue histology and blood cell binding panel has already been examined for hPAM4 IgG and for an anti-CEA× anti-HSG bsMAb that is entering clinical trials. hPAM4 binding was restricted to very weak binding to the urinary bladder and stomach in ⅓ specimens (no binding was seen in vivo), and no binding to normal tissues was attributed to the anti-CEA×anti-HSG bsMAb. Furthermore, in vitro studies against cell lines bearing the H1 and H2 histamine receptors showed no antagonistic or agonistic activity with the IMP-288 di-HSG peptide, and animal studies in 2 different species showed no pharmacologic activity of the peptide related to the histamine component at doses 20,000 times higher than that used for imaging. Thus, the HSG-histamine derivative does not have pharmacologic activity.

Biodistribution, Targeting and Dosage Studies of TF10 Bispecific Antibody

The biodistribution and tumor targeting of TF10 with increasing TF10 doses is determined. These studies provide basic Pk data for TF10 over a range of doses. The primary dose range simulates human equivalent doses (HED) between 1.0 to 50 mg given to a 70 kg patient. Based on FDA guidelines for converting a dose given to an animal to a HED [i.e., (mg/kg in a mouse/12.3)=mg/kg HED], a 1 mg (6.37 nmol) TF10 dose given to a 70 kg human would be equivalent to a 3.5 μg (0.022 nmol) dose in a 20 g mouse.

Briefly, animals are given iv injections of 3.5, 17.5, 35, and 70 TF10 (trace [125]I-TF10 added). Animals given 17.5, 35, and 70 μg doses (HED=1, 5, 10 and 20 mg) are necropsied at 1, 6, 16, 48, and 72 h (n=5 per observation; total N=75 animals/cell line). Studies with the current lot of TF10 have indicated a very rapid clearance in mice, similar to that of the TF2 anti-CEA construct described above.

Pk studies are also performed with [131]I-TF10 in rabbits. Prior studies with TF2 anti-CEA bsMAb have indicated that rabbits might better predict the Pk behavior that is observed in patients, since they clear humanized anti-CEA IgG in an identical manner as that found in patients, while mice clear humanized IgG at a faster rate. These studies would involve 4 rabbits, 2 given a 5-mg HED and 2 given a 20-mg HED of TF10 spiked with [131]I-TF10 (~700 μCi). Rabbits are bled at 5 min, 1, 3, 6, 24, 48, 72, 96, 120, and 168 h. Whole-body images are also taken using an ADAC Solus gamma camera equipped with a high-energy collimator. An $^{131}$I-standard (~20 μCi in a 10 mL syringe) is placed in the field of view with each rabbit during each imaging session taken at 3, 24, 48, 120, and 168 h. The standard is then used to provide semi-quantitative data on the distribution of [131]I-TF10.

Imaging Studies Using Pretargeting with TF2 and TF10 Bispecific Antibodies and Labeled Peptides The following studies demonstrate the feasibility of in vivo imaging using the pretargeting technique with bispecific antibodies and labeled peptides. While the images were not obtained using an $^{18}$F-metal labeled peptide as described above, the pretargeting technique with bispecific antibodies may be generally adapted to use with any type of label. Thus, the studies are representative of results that would be obtained using the claimed F-18 labeled peptides.

Figure 20:
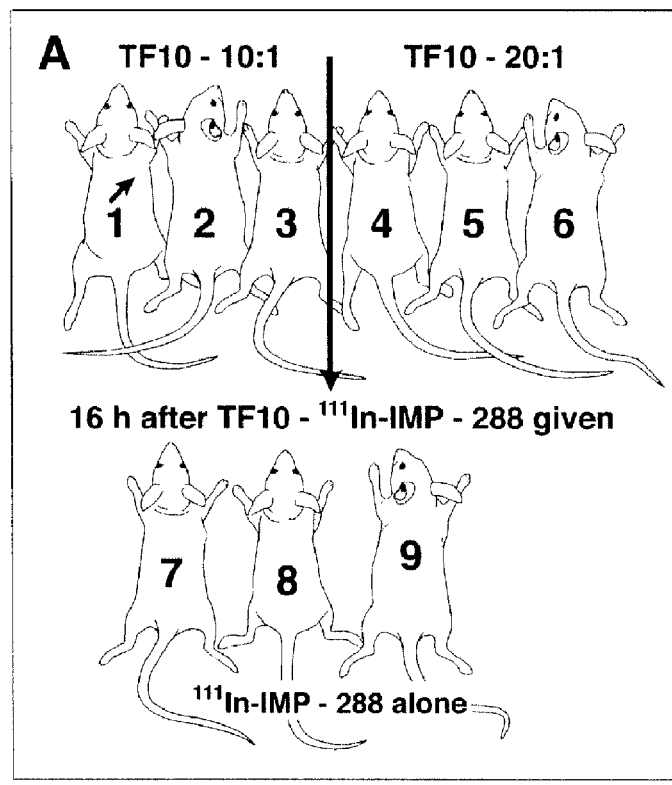
FIG. 20. In vivo imaging of tumors using an $^{111}$In-labeled diHSG peptide (IMP 288) with or without pretargeting TF10 bispecific anti-MUC 1 antibody.
Figure 20:
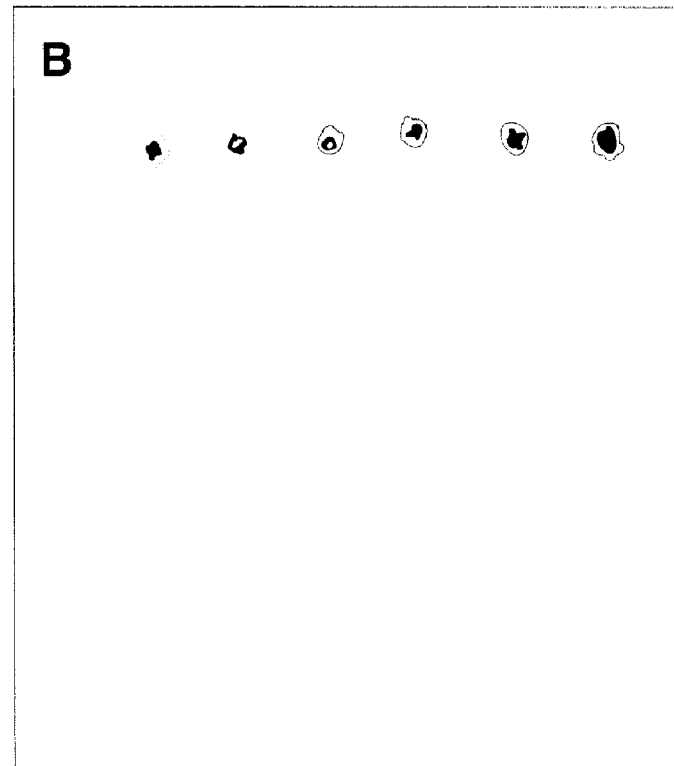
Figure 21:
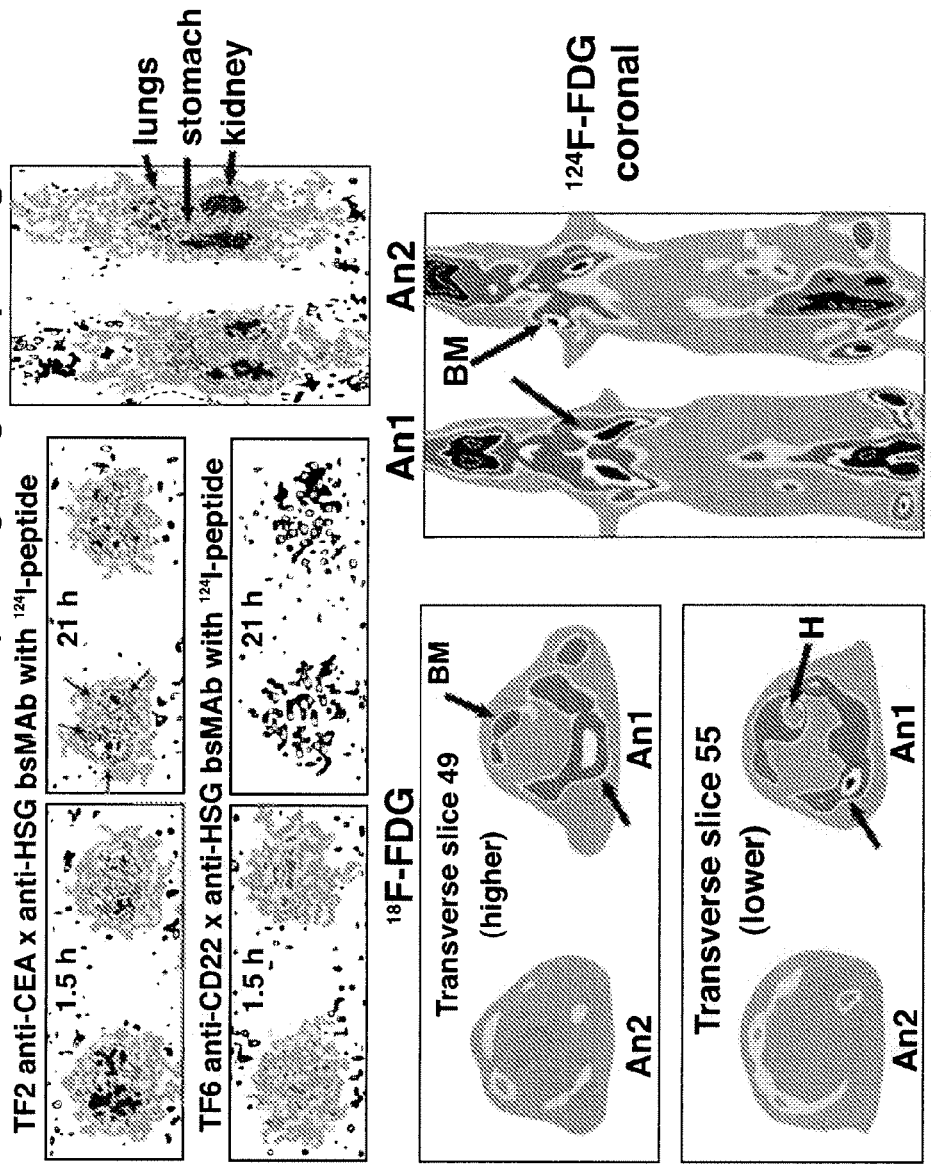
FIG. 21. PET imaging of micrometastatic human colon cancer in lungs of nude mice, using [124]I-labeled peptide and pretargeting with TF2 bispecific anti-CEA antibody.
Figure 22:
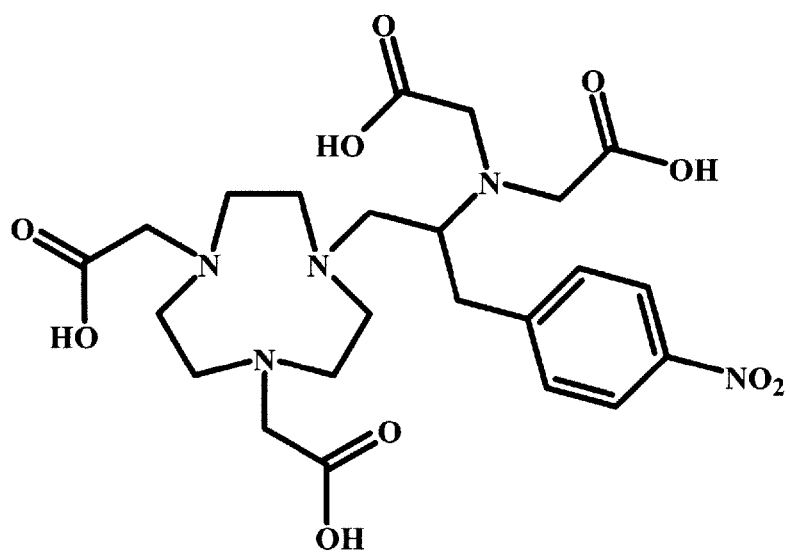
FIG. 22A-22D. Additional exemplary chelating moieties for use with F-18 labeling.
Figure 22:
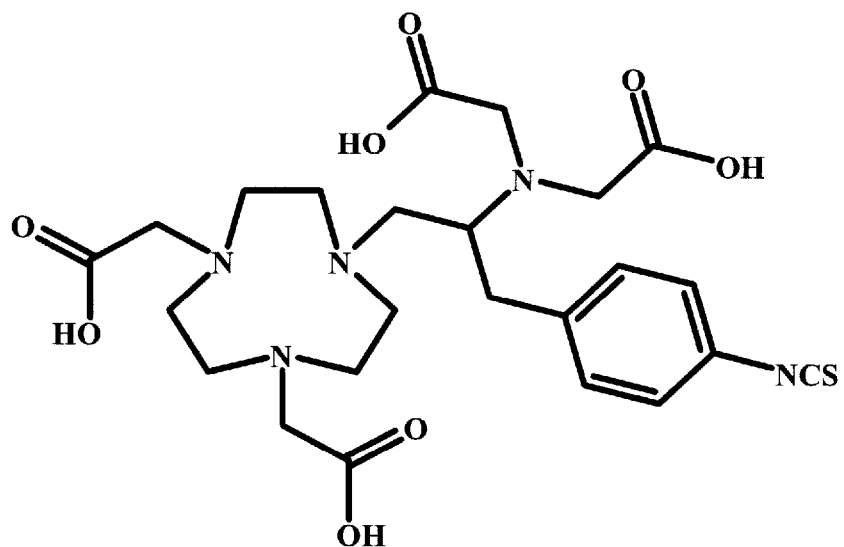
Figure 22:
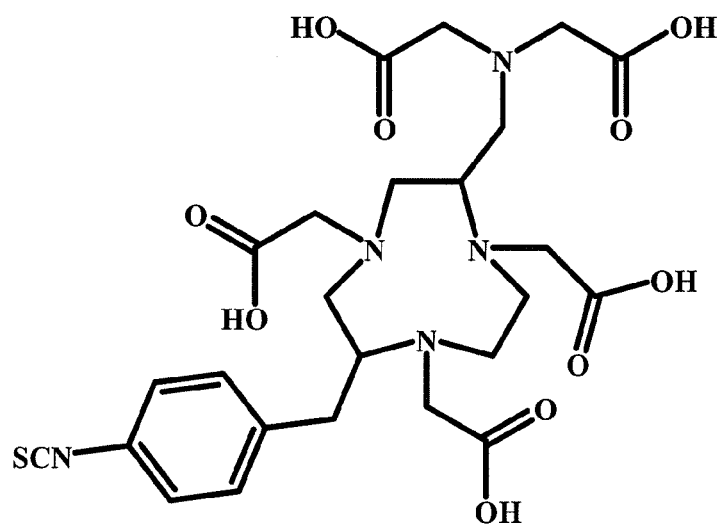
Figure 22:
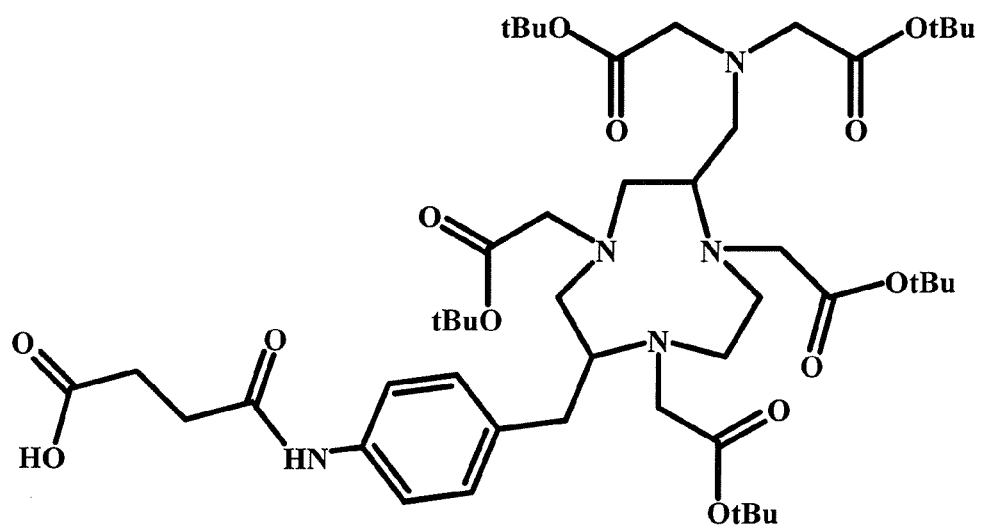

FIG. 20 and FIG. 21 show examples of how clearly delineated tumors can be detected in animal models using a bsMAb pretargeting method, with an $^{111}$In-labeled di-HSG peptide, IMP-288. In FIG. 20, nude mice bearing 0.2 to 0.3 g human pancreatic cancer xenografts were imaged, using pretargeting with TF10 and $^{111}$In-IMP-288 peptide. The six animals in the top of the Figure received 2 different doses of TF10 (10:1 and 20:1 mole ratio to the moles of peptide given), and the next day they were given an $^{111}$In-labeled diHSG peptide (IMP 288). The 3 other animals received only the $^{111}$In-IMP-288 (no pretargeting). The images were taken 3 h after the injection of the labeled peptide and show clear localization of 0.2-0.3 g tumors in the pretargeted animals, with no localization in the animals given the $^{111}$In-peptide alone.

In this study, tumor uptake averaged 20-25% ID/g with tumor/blood ratios exceeding 2000:1, tumor/liver ratios of 170:1, and tumor/kidney ratios of 18/1. Since tumor uptake shown in the Examples above for the Al-$^{18}$F-labeled IMP 449 averaged only about 4-5% ID/g in the same CaPan1 xenograft model, it is believed the lower uptake with $^{18}$F-labeled peptide merely reflects the lower specific activity of the Al-$^{18}$F-labeled IMP 449. Nevertheless, the Al-$^{18}$F-IMP 449 data show an extraordinary potential for the pretargeted, fluorinated peptide that when combined with the specificity of the TF10 bsMAb would be an excellent tool for imaging pancreatic or other cancers. The biodistribution data for $^{18}$F-labeled peptides far exceed the targeting ability of directly radiolabeled antibodies and small engineered antibody constructs directly labeled with $^{18}$F (Cai et al., J. Nucl. Med. 48: 304-310, 2007).

The data shown in FIG. 21 further highlights the sensitivity of the pretargeting method for detecting cancer. Here, a panel of microPET images was obtained from nude mice injected intravenously with a human colon cancer cell line and bearing 0.2-0.3 mm micrometastatic tumors in the lungs. Animals were administered the anti-CEA bsMAb TF2, followed with a pretargeted $^{124}$I-labeled peptide. The images show intense uptake in both the transverse and coronal sections at 1.5 h that persisted even at 21 h. The coronal section is a more posterior view to illustrate that the $^{124}$I-peptide was also seen in the stomach and kidneys 1.5 h after its injection. The images show what appear to be individual lesions in the lungs (arrows) that when necropsied were no larger than 0.3 mm in diameter (top panel, transverse sections through the chest) (Sharkey et al., Radiology, 246(2): 497-507, 2008). A control animal pretargeted with an anti-CD22 TF6 bsMAb and given the same $^{124}$I-labeled peptide (left side, middle panel) is shown to illustrate the specificity of the localization by, in this case, an anti-CEA bsMAb. The coronal section of the anti-CEA-pretargeted animals shows the uptake in the chest, as well as in the kidneys and some activity in the stomach. Significantly, the same sized lesions in the lungs were not seen in animals given $^{18}$F-FDG. Thus, use of pretargeting antibodies provides greater specificity and sensitivity of detection comparing to the standard F-18-labeled fluorodeoxyglucose probe currently used for PET imaging of cancer.

These data further demonstrate the feasibility of imaging using pretargeting with bispecific antibodies and $^{18}$F-labeled peptides.

Example 13

Synthesis of Folic Acid NOTA Conjugate

Folic acid is activated as described (Wang et. al. Bioconjugate Chem. 1996, 7, 56-62.) and conjugated to Boc-NH—CH$_2$—CH$_2$—NH$_2$. The conjugate is purified by chromatography. The Boc group is then removed by treatment with TFA. The amino folate derivative is then mixed with p-SCN-Bn-NOTA (Macrocyclics) in a carbonate buffer. The product is then purified by HPLC. The folate-NOTA derivative is labeled with Al-$^{18}$F as described in Example 10 and then HPLC purified. The $^{18}$F-labeled folate is injected i.v. into a subject and successfully used to image the distribution of folate receptors, for example in cancer or inflammatory diseases (see, e.g., Ke et al., Advanced Drug Delivery Reviews, 56:1143-60, 2004).

Example 14

Pretargeted PET Imaging in Humans

A patient (1.7 m$^2$ body surface area) with a suspected recurrent tumor is injected with 17 mg of bispecific monoclonal antibody (bsMAb). The bsMAb is allowed to localize to the target and clear from the blood. The F-18 labeled peptide (5-10 mCi on 5.7×10$^{-9}$ mol) is injected when 99% of the bsMab has cleared from the blood. PET imaging shows the presence of micrometastatic tumors.

Example 15

Imaging of Angiogenesis Receptors by F-18 Labeling

Labeled Arg-Gly-Asp (RGD) peptides have been used for imaging of angiogenesis, for example in ischemic tissues, where $\alpha_v\beta_3$ integrin is involved. (Jeong et al., J. Nucl. Med. 2008, Apr. 15 epub). RGD is conjugated to SCN-Bz-NOTA according to Jeong et al. (2008). Al-$^{18}$F is attached to the NOTA-derivatized RGD peptide as described in Example 10 above, by mixing aluminum stock solution with F-18 and the derivatized RGD peptide and heating at 110° C. for 15 min, using an excess of peptide to drive the labeling reaction towards completion as disclosed in Example 10. The F-18 labeled RGD peptide is used for in vivo biodistribution and PET imaging as disclosed in Jeong et al. (2008). The Al-$^{18}$F conjugate of RGD-NOTA is taken up into ischemic tissues and provides PET imaging of angiogenesis.

Example 16

Imaging of Tumors Using F-18 Labeled Bombesin

A NOTA-conjugated bombesin derivative (NOTA-8-Aoc-BBN(7-14)NH$_2$) is prepared according to Prasanphanich et at (Proc. Natl. Acad. Sci. USA 2007, 104:12462-467). The NOTA-bombesin derivative is labeled with Al-$^{18}$F according to Example 10 above. The F-18 labeled bombesin derivative is separated from unlabeled bombesin on an OASIS® column (Waters, Milford, Mass.), as described in Example 10. The Al-$^{18}$F labeled NOTA-bombesin conjugate is successfully used for PET imaging of gastrin-releasing peptide receptor expressing tumors, according to Prasanphanich et al. (2007).

Example 17

Imaging of Tumors Using F-18 Labeled Targetable Conjugates

NOTA derivatives of peptides, polypeptides, proteins, carbohydrates, cytokines, hormones or cell receptor-binding agents are prepared according to U.S. Pat. No. 7,011,816 (incorporated herein by reference in its entirety). The NOTA-derivatized targetable conjugates are labeled with Al-$^{18}$F as disclosed in Example 10. The conjugates are administered in vivo and successfully used for F-18 PET imaging of tumors.

Example 18

Imaging of Tumors Using Bispecific Antibodies

Bispecific antibodies having at least one arm that specifically binds a targeted tissue and at least one other arm that specifically binds a targetable conjugate are prepared according to U.S. Pat. No. 7,052,872, incorporated herein by reference in its entirety. The targetable conjugate comprises one or more NOTA chelating moieties. The targetable conjugate is labeled with Al-$^{18}$F as described in Example 10. A subject with a disease condition is injected with bispecific antibody. After allowing a sufficient time for free bispecific antibody to clear from the circulation, the subject is injected with F-18 labeled targetable conjugate. Imaging of the distribution of the F-18 label is performed by PET scanning.

In another exemplary embodiment, humanized or chimeric internalizing anti-CD74 antibody is prepared as described in U.S. Pat. No. 7,312,318. The p-SCN-bn-NOTA precursor is labeled with Al-$^{18}$F as described in Example 7. The Al-$^{18}$F NOTA is then conjugated to the antibody using standard techniques. Upon i.v. injection into a subject with a CD74-expressing tumor, the anti-CD74 antibody localizes to the tumor, allowing imaging of the tumor by PET scanning. In alternative embodiments, F-18 labeled antibodies are prepared using the alpha-fetoprotein binding antibody Immu31, hPAM4, cPAM4, RS7, anti-CD20, anti-CD19, anti-CEA and anti-CD22, as described in U.S. Pat. Nos. 7,300,655; 7,282,567; 7,238,786; 7,238,785; 7,151,164; 7,109,304; 6,676,924; 6,306,393 and 6,183,744. The antibodies are conjugated to NOTA using standard techniques and labeled with Al-$^{18}$F as described for anti-CD74 antibody. The F-18 labeled antibodies are injected into subjects and provide successful imaging of tumors by PET scanning.

Example 19

Use of $^{18}$F-Labeled NOTA for Renal Flow Imaging

Aluminum stock solution (20 µL 0.05 M in pH 4 NaOAc buffer) is mixed with 200 µL of QMA purified F-18 (as in Example 10). The AlF-18 solution is then mixed with 500 µL pH 4, 0.2 M NOTA and heated for 15 min. The sample is then diluted in 5 mL PBS for injection. The F-18 labeled NOTA is used directly for successful renal flow imaging.

Example 20

Further Peptide Labeling Studies with Al-$^{18}$F

IMP 460 NODA-GA-D-Ala-D-Lys(HSG)-D-Tyr-D-Lys(HSG)-NH$_2$ was synthesized in a similar manner as described above for IMP 361. The NODA-Ga ligand was purchased from Chematech and attached on the peptide synthesizer like the other amino acids. The crude peptide was purified to afford the desired peptide MH$^+$ 1366.

Radiolabeling of IMP 460

IMP 460 (0.0020 g) was dissolved in 732 µL, pH 4, 0.1 M NaOAc. The F-18 was purified as described in Example 10, neutralized with glacial acetic acid and mixed with the Al solution. The peptide solution, 20 µL was then added and the solution was heated at 99° C. for 25 min. The crude product was then purified on a Waters HLB column as described above. The Al-F-18 labeled peptide was in the 1:1 EtOH/H$_2$O column eluent. The reverse phase HPLC trace in 0.1% TFA buffers showed a clean single HPLC peak at the expected location for the labeled peptide.

Example 21

Carbohydrate Labeling

A NOTA thiosemicarbazide derivative is prepared by reacting the p-SCN-bn-NOTA with hydrazine and then purifying the ligand by HPLC. Al-F-18 is prepared as described in Example 10 and the Al-F-18 is added to the NOTA thiosemicarbazide and heated for 15 min. Optionally the Al-F-18-thiosemicarbazide complex is purified by HPLC. The Al-F-18-thiosemicarbazide is conjugated to oxidized carbohydrates by known methods. The F-18 labeled carbohydrate is successfully used for imaging studies using PET scanning.

Example 22

Lipid Labeling

A lipid comprising an aldehyde is conjugated to the Al-F-18 NOTA thiosemicarbazide of Example 21 and the F-18 labeled lipid is used for successful imaging studies using PET scanning.

In an alternative embodiment, a lipid comprising an amino group is reacted with p-SCN-bn-NOTA. The NOTA-labeled lipid is reacted with Al-F-18 as described in the Examples above. The F-18 labeled lipid is used for successful imaging studies using PET scanning.

Example 23

Aptamer Labeling

An aptamer comprising an aldehyde is conjugated to the Al-F-18 NOTA thiosemicarbazide of Example 21. The F-18 labeled aptamer is administered to a subject and used for successful imaging studies using PET scanning.

What is claimed is:

1. An F-18 labeled molecule comprising:
   a) a complex between F-18 and a metal selected from the group consisting of aluminum, gallium, indium, lutetium and thallium; and
   b) a chelating moiety attached to the molecule, wherein the F-18-metal complex is bound to the chelating moiety.

2. The F-18 labeled molecule of claim 1, wherein the molecule is a protein or peptide.

3. The F-18 labeled molecule of claim 2, wherein the protein or peptide is an antibody, an antibody fragment, a bispecific antibody, a targetable construct peptide or a receptor-binding ligand.

4. The F-18 labeled molecule of claim 3, wherein antibody, antibody fragment or bispecific antibody binds to a tumor-associated antigen selected from the group consisting of colon-specific antigen-p (CSAp), carcinoembryonic antigen (CEA), CD4, CD5, CD8, CD14, CD15, CD19, CD20, CD21, CD22, CD23, CD25, CD30, CD45, CD66a-d, CD67, CD74, CD79a, CD80, CD138, HLA-DR, Ia, Ii, MUC 1, MUC 2, MUC 3, MUC 4, NCA, EGFR, HER 2/neu receptor, TAG-72, EGP-1, EGP-2, A3, KS-1, Le(y), S100, PSMA, PSA, tenascin, folate receptor, VEGFR, EGFR, PDGFR, FGFR, P1GF, ILGF-1, necrosis antigens, IL-2, IL-6, T101 and MAGE.

5. The F-18 labeled molecule of claim 3, wherein the antibody is selected from the group consisting of LL1, LL2, RFB4, Immu31, PAM4, KC4, RS7, A19, A20, MN-14, Mu-9, MN-3, MN-15, TAG-72, Tn, J591, G250 and L243.

6. The F-18 labeled molecule of claim 1, wherein the metal is aluminum.

7. The F-18 labeled molecule of claim 1, wherein the chelating moiety is NOTA, DTPA, 2-benzyl-DTPA, TETA, NETA, a macrocyclic polyether, a porphyrin, Tscg-Cys or Tsca-Cys.

8. The F-18 labeled molecule of claim 1, wherein the chelating moiety is NOTA.

9. The F-18 labeled molecule of claim 1, wherein the F-18 labeled molecule is stable in human serum at 37° C. for at least one hour.

10. The F-18 labeled molecule of claim 1, wherein the F-18 labeled molecule is stable in human serum at 37° C. for at least four hours.

11. A kit for F-18 labeling of a molecule comprising:
    a) a metal selected from the group consisting of aluminum, gallium, indium, lutetium and thallium, wherein the metal forms a complex with F-18; and
    b) a molecule comprising one or more chelating moieties that bind to the F-18-metal complex.

12. The kit of claim 11, further comprising one or more buffers.

13. The kit of claim 11, further comprising a radiolysis protection agent.

14. The kit of claim 13, wherein the radiolysis protection agent is ascorbic acid.

15. The kit of claim 11, wherein the molecule is a protein or peptide.

16. The kit of claim 15, wherein the protein or peptide is an antibody, an antibody fragment, a bispecific antibody, a targetable construct peptide or a receptor-binding ligand.

17. The kit of claim 16, wherein antibody, antibody fragment or bispecific antibody binds to a tumor-associated antigen selected from the group consisting of colon-specific antigen-p (CSAp), carcinoembryonic antigen (CEA), CD4, CD5, CD8, CD14, CD15, CD19, CD20, CD21, CD22, CD23, CD25, CD30, CD45, CD66a-d, CD67, CD74, CD79a, CD80, CD138, HLA-DR, Ia, Ii, MUC 1, MUC 2, MUC 3, MUC 4, NCA, EGFR, HER 2/neu receptor, TAG-72, EGP-1, EGP-2, A3, KS-1, Le(y), S100, PSMA, PSA, tenascin, folate receptor, VEGFR, EGFR, PDGFR, FGFR, P1GF, ILGF-1, necrosis antigens, IL-2, IL-6, T101 and MAGE.

18. The kit of claim 16, wherein the antibody is selected from the group consisting of LL1, LL2, RFB4, Immu31, PAM4, KC4, RS7, A19, A20, MN-14, Mu-9, MN-3, MN-15, TAG-72, Tn, J591, G250 and L243.

19. The kit of claim 11, wherein the metal is aluminum.

20. The kit of claim 11, wherein the chelating moiety is NOTA, DTPA, 2-benzyl-DTPA, TETA, NETA, a macrocyclic polyether, a porphyrin, Tscg-Cys or Tsca-Cys.

21. The kit of claim 11, wherein the chelating moiety is NOTA.

22. The kit of claim 11, wherein the F-18 labeled molecule is stable in human serum at 37° C. for at least one hour.

23. The kit of claim 11, wherein the F-18 labeled molecule is stable in human serum at 37° C. for at least four hours.

* * * * *